(12) United States Patent
Nishide et al.

(10) Patent No.: US 8,653,277 B2
(45) Date of Patent: Feb. 18, 2014

(54) FUNGICIDAL COMPOSITION AND METHOD FOR CONTROLLING PLANT DISEASES

(75) Inventors: Hisaya Nishide, Kusatsu (JP); Shigeyuki Nishimura, Kusatsu (JP); Shigeru Mitani, Kusatsu (JP); Koji Minamida, Kusatsu (JP); Fumio Kanamori, Kusatsu (JP); Munekazu Ogawa, Kusatsu (JP); Shigehisa Kanbayashi, Kusatsu (JP); Toyoshi Tanimura, Kusatsu (JP); Koji Higuchi, Kusatsu (JP); Hidemasa Kominami, Kusatsu (JP); Tomohiro Okamoto, Kusatsu (JP); Akihiro Nishimura, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 503 days.

(21) Appl. No.: 12/474,837

(22) Filed: May 29, 2009

(65) Prior Publication Data

US 2009/0247763 A1    Oct. 1, 2009

Related U.S. Application Data

(60) Division of application No. 11/414,401, filed on May 1, 2006, now abandoned, which is a continuation of application No. PCT/JP2004/016156, filed on Oct. 29, 2004.

(30) Foreign Application Priority Data

| | | |
|---|---|---|
| Oct. 31, 2003 | (JP) | 2003-371863 |
| Jan. 14, 2004 | (JP) | 2004-006355 |
| Jul. 16, 2004 | (JP) | 2004-210174 |

(51) Int. Cl.
   *C07D 213/50*    (2006.01)

(52) U.S. Cl.
   USPC .......................... 546/318; 546/314

(58) Field of Classification Search
   USPC .................................. 546/314, 318
   See application file for complete search history.

(56) References Cited

U.S. PATENT DOCUMENTS

| | | | | |
|---|---|---|---|---|
| 4,523,018 | A | * | 6/1985 | Kumagae et al. ............. 546/315 |
| 4,853,481 | A | * | 8/1989 | Henkelmann et al. ......... 562/460 |
| 5,962,731 | A | * | 10/1999 | Boehm et al. ................. 562/460 |
| 6,770,662 | B2 | | 8/2004 | Nishide et al. |
| 2003/0216444 | A1 | | 11/2003 | Nishide et al. |
| 2006/0089390 | A1 | | 4/2006 | Nishide et al. |
| 2006/0194849 | A1 | | 8/2006 | Nishide et al. |

FOREIGN PATENT DOCUMENTS

| | | |
|---|---|---|
| CN | 1440389 A | 9/2003 |
| EP | 0 032 516 A1 | 7/1981 |
| EP | 0032516 * | 7/1981 |
| EP | 0 254 241 | 1/1988 |
| JP | 2002-356474 | 12/2002 |
| WO | WO 02/02527 * | 1/2002 |
| WO | WO02/02527 | 1/2002 |

OTHER PUBLICATIONS

Bhaysar et al. (Man-Made Textiles in India, 1989, 32(3); 103-106).*
Faul et al. (J. Org. Chem. 2001, 66, 5772-5782).*
Bhavsar et al. (Man-Made Textiles in India, 1989, 32(2); 55-58).*
Katritzky et al. (Comprehensive Organic Functional Group Transformations, vol. 5, First Edition, Elsevier Science (1995); p. 13).*
Gore et al. (J. Org. Chem. (1955) 55(2), pp. 229-281).*
Practical Dictionary of Organic Chemistry, Higher Education Publishing House, edited by Gao Hongbin, Jul. 1997, cover page and pp. 531-534.
U.S. Appl. No. 13/002,361, filed Jan. 3, 2011, Ogawa, et al.
European Search Report in corresponding Supplementary European Application No. 04793257.9 dated May 18, 2011.
D. Cameron, et al., "Synthesis of Azaanthraquinones: Homolytic Substitution of Pyridines*", Aust. J. Chem., 1982, vol. 35 No. 7, pp. 1451-1468.

(Continued)

*Primary Examiner* — Noble Jarrell
*Assistant Examiner* — Valerie Rodriguez-Garcia
(74) *Attorney, Agent, or Firm* — Oblon, Spivak, McClelland, Maier & Neustadt, L.L.P.

(57) ABSTRACT

It is to provide a fungicidal composition having stable and high fungicidal effects against cultivated crops infected with plant diseases resulting from plant diseases.
A fungicidal composition containing as active ingredients (a) a benzoylpyridine derivative represented by the formula (I) or its salt:

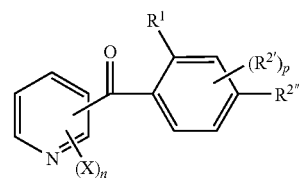

(wherein X is a halogen atom, a nitro group, a substitutable hydrocarbon group, a substitutable alkoxy group, a substitutable aryloxy group, a substitutable cycloalkoxy group, a hydroxyl group, a substitutable alkylthio group, a cyano group, a carboxyl group which may be esterified or amidated, or a substitutable amino group, n is 1, 2, 3 or 4; $R^1$ is a substitutable alkyl group, $R^{2'}$ is a substitutable alkyl group, a substitutable alkoxy group, a substitutable aryloxy group, a substitutable cycloalkoxy group or a hydroxyl group, p is 1, 2 or 3, and $R^{2''}$ is a substitutable alkoxy group or a hydroxyl group, provided that at least two of $R^{2'}$ and $R^{2''}$ may form a condensed ring containing an oxygen atom) and (b) at least one another fungicide.

8 Claims, No Drawings

(56) References Cited

OTHER PUBLICATIONS

E. Langhals, et al., "Eine Einfache Neue Synthese der Fusarinsäure und Anderer 5-Alkyl-2-pyridincarbonsäuren", Liebigs Ann. Chem., 1982, No. 5, pp. 930-945.

J. Backvall, et al., "Synthesis of 3-Aryl-3-pyridylallylamines Related to Zimelidine via Palladium-Catalyzed Amination", J. Org. Chem., 1981, vol. 46, No. 17, pp. 3479-3483. XP 000608977.

R. Wolffenstein, et al., "Die Friedel-Craftssche Keton-Synthese in der Pyridin-Reihe", Berichte Der Deutschen Chemischen Gesellschaft, 1915, vol. 48, No. 2, pp. 2043-2049. XP 007918582.

\* cited by examiner ically excellent fungicidal
FUNGICIDAL COMPOSITION AND METHOD FOR CONTROLLING PLANT DISEASES This application is a Divisional of U.S. application Ser. No. 11/414,401, filed on May 1, 2006, which is a Continuation of International Application No. PCT/JP04/16156, filed on Oct. 29, 2004.

TECHNICAL FIELD

The present invention relates to a fungicidal composition useful as an agricultural and horticultural fungicide having remarkably improved preventive and/or curative effects against plant diseases, and a method for controlling plant diseases by using such a composition.

BACKGROUND ART

WO02/2527 discloses that a benzoylpyridine derivative which is an active ingredient of the fungicidal composition in the present invention is useful as a fungicide and may be used in combination with another fungicide as the case required. However, it has not been known that the composition of the present invention has a remarkably excellent fungicidal effect.
Patent Document 1: WO02/2527

DISCLOSURE OF THE INVENTION

Problems that the Invention is to Solve

Each of benzoylpyridine derivatives represented by the formula (I) given hereinafter, may have an inadequate controlling effect against a specific plant disease, its residual effect may last only a relatively short time or its rainfastness may be weak, and it has only an inadequate controlling effect against plant diseases practically depending upon the application site.

Means of Solving the Problems

The present inventors have conducted a research to solve the above problems and as a result, found that when a benzoylpyridine derivative represented by the formula (I) given hereinafter and a specific fungicide are used in combination, an unexpectedly excellent fungicidal effect can be obtained as compared with a case where the respective compounds are used alone.

Namely, the present invention provides a fungicidal composition containing as active ingredients (a) a benzoylpyridine derivative represented by the formula (I) or its salt:

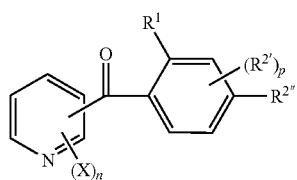

(wherein X is a halogen atom, a nitro group, a substitutable hydrocarbon group, a substitutable alkoxy group, a substitutable aryloxy group, a substitutable cycloalkoxy group, a hydroxyl group, a substitutable alkylthio group, a cyano group, a carboxyl group which may be esterified or amidated, or a substitutable amino group, n is 1, 2, 3 or 4; $R^1$ is a substitutable alkyl group, $R^2$ is a substitutable alkyl group, a substitutable alkoxy group, a substitutable aryloxy group, a substitutable cycloalkoxy group or a hydroxyl group, p is 1, 2 or 3, and $R^{2''}$ is a substitutable alkoxy group or a hydroxyl group, provided that at least two of $R^{2'}$ and $R^{2''}$ may form a condensed ring containing an oxygen atom) and (b) at least one fungicide selected from the group consisting of a strobilurin compound, an azole compound, a morpholine compound, a pyrimidinamine compound, a guanidine compound, an organic chlorine compound, an imidazole compound, an antibiotic, a pyridinamine compound, a quinoxaline compound, a dithiocarbamate compound, a cyanoacetamide compound, a phenylamide compound, a sulfenic acid compound, a copper compound, an isoxazole compound, an organophosphorus compound, a N-halogenothioalkyl compound, a dicarboxylmide compound, a benzanilide compound, piperazine compound, a pyridine compound, a carbinol compound, a piperidine compound, an organotin compound, an urea compound, a cynnamic acid compound, a phenyl carbamate compound, a cyanopyrrole compound, an oxazolidinone compound, a thiazole carboxyamide compound, a silyl amide compound, an aminoacid amidecarbamate compound, an imidazolidine compound, a hydroxyanilide compound, an oxime ether compound, a phenoxyamide compound, a benzophenone compound, Isoprothiolane, Pyroquilon, Dichlomezine, Quinoxyfen, Propamocarb Hydrochloride, Chloropicrin, Dazomet, Metam-sodium, Nicobifen, Diclocymet and Proquinazid. The present invention further provides a method for controlling plant diseases, which comprises applying the above fungicidal composition to plants.

In the formula (I), the halogen atom is fluorine, chlorine, bromine or iodine, and it may, for example, be preferably fluorine, chlorine or bromine.

The hydrocarbon moiety in the substitutable hydrocarbon group in the formula (I) may, for example, be a $C_{1-6}$ alkyl (such as methyl, ethyl, propyl, isopropyl, butyl, isobutyl or t-butyl), a $C_{2-6}$ alkenyl (such as vinyl, allyl, isopropenyl or 3-methyl-2-butenyl), a $C_{2-6}$ alkynyl (such as ethynyl, 1-propynyl or 2-propynyl), a $C_{3-6}$ cycloalkyl (such as cyclopropyl, cyclopentyl or cyclohexyl) or a $C_{6-10}$ aryl. Further, the secondary substituent in the substitutable hydrocarbon group may, for example, be the same or different one to five substituents selected from the group consisting of aryl, aryloxy, hydroxy, nitro, nitroxy, halogen (such as fluorine, chlorine, bromine or iodine), haloalkoxy (such as a $C_{1-4}$ haloalkoxy, for instance $CF_3O$ or $HCF_2O$), cycloalkyl, amino, alkylthio and cyano. Among these substitutable hydrocarbon groups, a substitutable alkyl group is preferred, and an alkyl group is particularly preferred. Further, among alkyl groups, a $C_{1-4}$ alkyl group is most preferred.

The alkyl moiety in the substitutable alkyl group, the substitutable alkoxy group and the substitutable alkylthio group in the formula (I) is preferably a $C_{1-6}$ alkyl (such as methyl, ethyl, propyl, isopropyl, butyl, isobutyl or t-butyl), particularly preferably a $C_{1-4}$ alkyl. Further, the secondary substituent in these substituents may be the same or different one to five substituents selected from the group consisting of aryl, aryloxy, hydroxy, nitro, nitroxy, halogen (such as fluorine, chlorine, bromine or iodine), haloalkoxy (such as a $C_{1-4}$ haloalkoxy, for instance $CF_3O$ or $HCF_2O$), cycloalkyl, amino, alkylthio and cyano. Among such substituents having an alkyl moiety, a non-substituted substituent is preferred, a $C_{1-4}$ alkyl is particularly preferred, and methyl is most preferred.

The aryl moiety in the substitutable aryloxy group in the formula (I) may be phenyl, or a condensed polycyclic group such as naphthyl, but it is preferably phenyl. Further, the secondary substituent, for instance substitutable group may, for example, be halogen, alkyl, alkoxy or hydroxy.

The cycloalkyl moiety in the substitutable cycloalkoxy group in the formula (I) consists of three to ten carbons, and it may, for example, be a monocyclic group such as cyclopropyl, cyclobutyl, cyclopentyl, cyclohexyl or cyclooctyl, or a condensed polycyclic group, but it is preferably a monocyclic group. Further, the secondary substituent in these substitutable groups may, for example, be halogen, alkyl, alkoxy or hydroxy. Among the cycloalkoxy moieties, cyclohexyloxy is most preferred.

The carboxyl group which may be esterified or amidated in the formula (I) may, for example, be a carboxyl group which may be esterified, such as a $C_{1-6}$ alkoxycarbonyl group (such as a methoxycarbonyl group, an ethoxycarbonyl group, a propoxycarbonyl group, an isopropoxycarbonyl group, a butoxycarbonyl group, an isobutoxycarbonyl group or a t-butoxycarbonyl group), a nitroxy $C_{1-4}$ alkoxyaminocarbonyl group (such as a 2-nitroxyethoxycarbonyl group or a 3-nitroxypropoxycarbonyl group) or a phenyl $C_{1-4}$ alkoxycarbonyl group (such as a benzyloxycarbonyl group or a phenethyloxycarbonyl group); or a carboxyl group which may be amidated, such as a carbamoyl group, a $C_{1-6}$ monoalkylaminocarbonyl group (such as a methylaminocarbonyl group, an ethyaminocarbonyl group, a propylaminocarbonyl group, an isopropylaminocarbonyl group, a butylaminocarbonyl group, an isobutylaminocarbonyl group or a t-butylaminocarbonyl group), a di $C_{1-6}$ alkylaminocarbonyl group (such as a dimethylaminocarbonyl group, a diethylaminocarbonyl group, a dipropylaminocarbonyl group, a diisopropylaminocarbonyl group, a dibutylaminocarbonyl group or an isodibutylaminocarbonyl group), a nitroxy $C_{1-4}$ alkylaminocarbonyl group (such as a 2-nitroxyethylaminocarbonyl group or a 3-nitroxypropylaminocarbonyl group), a phenyl $C_{1-4}$ alkylaminocarbonyl group (such as a benzylaminocarbonyl group or a phenethylaminocarbonyl group), a $C_{3-6}$ cycloalkylaminocarbonyl group (such as a cyclopropylaminocarbonyl group, a cyclopentylaminocarbonyl group or a cyclohexylaminocarbonyl group), a cyclic aminocarbonyl group (such as a morpholinocarbonyl group, a piperidinocarbonyl group, a pyrrolidinocarbonyl group or a thiomorpholinocarbonyl group) or an aminocarbonyl group.

The substitutable amino group in the formula (I) may, for example, be an amino group; or an alkylamino group such as a monoalkylamino group or a dialkylamino group. The alkyl moiety in the alkylamino group is preferably a $C_{1-4}$ alkyl. Further, the secondary substituent in the substitutable amino group may be the same or different one to five substituents selected from aryl, aryloxy, hydroxy, nitro, nitroxy, halogen (such as fluorine, chlorine, bromine or iodine), haloalkoxy (such as a $C_{1-4}$ haloalkoxy group, for instance $CF_3O$ or $HCF_2O$), cycloalkyl, amino, alkylthio and cyano.

In the above secondary substituents in the above-mentioned respective substituents, the aryl moiety, the cycloalkyl moiety and the alkyl moiety are as defined for the respective substituents.

The compound represented by the formula (I) may form a salt together with an acidic substance, and it may form, for example, an inorganic acid salt such as a hydrochloride, a hydrobromide, a phosphate, a sulfate or a nitrate; or an organic acid salt such as an acetate, a benzoate, a p-toluenesulfonate, a methanesulfonate or a propanesulfonate.

The compounds represented by the formula (I) may be prepared by a production process as disclosed in WO02/2527. Further, they may be produced also by a method in accordance with Journal of Organic Chemistry, 58, 7832 (1993), European Journal of Organic Chemistry, 7, 1371-1376 (2001) or Preparation Examples given hereinafter.

The strobilurin compound may, for example, be Kresoxim-Methyl, Azoxystrobin, Metominofen, Trifloxystrobin, Picoxystrobin, Oryzastrobin, Dimoxystrobin or Fluoxastrobin. Among them, Kresoxim-Methyl and Azoxystrobin are preferred.

Kresoxim-Methyl is a compound disclosed in The Pesticide Manual (Twelfth Edition, BRITISH CROP PROTECTION COUNCIL), p. 568-569. Further, Azoxystrobin a compound disclosed in The Pesticide Manual (Twelfth Edition, BRITISH CROP PROTECTION COUNCIL), p. 54-55.

The azole compound may, for example, be Epoxiconazole, Triflumizole, Oxpoconazole fumarate, Tebuconazole, Imibenconazole, Tetraconazole, Triadimefon, Bitertanol, Etaconazole, Propiconazole, Penconazole, Flusilazole, Myclobutanil, Cyproconazole, Hexaconazole, Furconazole-cis, Prochloraz, Metconazole, Sipconazole, Prothioconazole, Simeconazole, Tricyclazole, Probenazole, Fluquinconazole or Triadimenol. Among them, Epoxiconazole, Triflumizole, Oxpoconazole fumarate, Tebuconazole, Imibenconazole, Tetraconazole, Cyproconazole, Metconazole, Fluquinconazole and Triadimenol are preferred.

Epoxiconazole is a compound disclosed in The Pesticide Manual (Twelfth Edition, BRITISH CROP PROTECTION COUNCIL), p. 349-350. Triflumizole is a compound disclosed in The Pesticide Manual (Twelfth Edition, BRITISH CROP PROTECTION COUNCIL), p. 940-941. Oxpoconazole fumarate is a compound disclosed in The Pesticide Manual (Twelfth Edition, BRITISH CROP PROTECTION COUNCIL), p. 699. Tebuconazole is a compound disclosed in The Pesticide Manual (Twelfth Edition, BRITISH CROP PROTECTION COUNCIL), p. 864-865. Imibenconazole is a compound disclosed in The Pesticide Manual (Twelfth Edition, BRITISH CROP PROTECTION COUNCIL), p. 535-536. Tetraconazole is a compound disclosed in The Pesticide Manual (Thirteenth Edition, BRITISH CROP PROTECTION COUNCIL), p. 945-946. Cyproconazole is a compound disclosed in The Pesticide Manual (Thirteenth Edition, BRITISH CROP PROTECTION COUNCIL), p. 248-249. Metconazole is a compound disclosed in The Pesticide Manual (Thirteenth Edition, BRITISH CROP PROTECTION COUNCIL), p. 643-644. Fluquinconazole is a compound disclosed in The Pesticide Manual (Thirteenth Edition, BRITISH CROP PROTECTION COUNCIL), p. 472-473. Triadimenol is a compound disclosed in The Pesticide Manual (Thirteenth Edition, BRITISH CROP PROTECTION COUNCIL), p. 987-989.

The morpholine compound may, for example, be Fenpropimorph or Spiroxamine. Fenpropimorph is a compound disclosed in The Pesticide Manual (Twelfth Edition, BRITISH CROP PROTECTION COUNCIL), p. 399-400. Spiroxamine is a compound disclosed in The Pesticide Manual (Twelfth Edition, BRITISH CROP PROTECTION COUNCIL), p. 842-843.

The pyrimidinamine compound may, for example, be Mepanipyrim, Pyrimethanil or Cyprodinil. Among them, Mepanipyrim is preferred. Mepanipyrim is a compound disclosed in The Pesticide Manual (Twelfth Edition, BRITISH CROP PROTECTION COUNCIL), p. 596-597.

The guanidine compound may, for example, be Iminoctadine. Iminoctadine is a compound disclosed in The Pesticide Manual (Twelfth Edition, BRITISH CROP PROTECTION COUNCIL), p. 539-541.

The organic chlorine compound may, for example, be Chlorothalonil, Fthalide or Quintozene. Among them, Chlorothalonil is preferred. Chlorothalonil is a compound disclosed in The Pesticide Manual (Twelfth Edition, BRITISH CROP PROTECTION COUNCIL), p. 168-169.

The imidazole compound may be Cyazofamid, Benomyl, Thiophanate-Methyl or Carbendazim. Among them, Cyazofamid is preferred. Cyazofamid is a compound disclosed in The Pesticide Manual (Twelfth Edition, BRITISH CROP PROTECTION COUNCIL), p. 523-524.

The antibiotic may, for example, be Polyoxins. Polyoxins is a compound disclosed in The Pesticide Manual (Twelfth Edition, BRITISH CROP PROTECTION COUNCIL), p. 752-754.

The pyridinamine compound may, for example, be Fluazinam.

The quinoxaline compound may, for example, be Quinomethionate.

The dithiocarbamate compound may, for example, be Maneb, Zineb, Mancozeb, Polycarbamate, Metiram or Propineb.

The cyanoacetamide compound may, for example, be Cymoxanil.

The phenylamide compound may, for example, be Metalaxyl, Metalaxyl M, Oxadixyl, Ofurace, Benalaxyl, Furalaxyl or Cyprofuram.

The sulfenic acid compound may, for example, be Dichlofluanid.

The copper compound may, for example, be Cupric hydroxide or Oxine Copper.

The isoxazole compound may, for example, be Hymexazol.

The organophosphorus compound may, for example, be Fosetyl-Al, Tolcofos-Methyl, S-benzyl O,O-diisopropylphosphorothioate, O-ethyl S,S-diphenylphosphorodithioate or aluminum ethyl hydrogen phosphonate.

The N-halogenothioalkyl compound may, for example, be Captan, Captafol or Folpet.

The dicarboxylmide compound may, for example, be Procymidone, Iprodione or Vinclozolin.

The benzanilide compound may, for example, be Flutolanil, Mepronil, Zoxamid or Tiadinil.

The piperazine compound may, for example, be Triforine.

The pyridine compound may, for example, be Pyrifenox.

The carbinol compound may, for example, be Fenarimol or Flutriafol.

The piperidine compound may, for example, be Fenpropidine. Fenpropidine is a compound disclosed in The Pesticide Manual (Thirteenth Edition, BRITISH CROP PROTECTION COUNCIL), p. 419-420.

The organotin compound may, for example, be Fentin Hydroxide or Fentin Acetate.

The urea compound may, for example, be Pencycuron.

The cinnamic acid compound may, for example, be Dimethomorph or Flumorph.

The phenyl carbamate compound may, for example, be Diethofencarb.

The cyanopyrrole compound may, for example, be Fludioxonil or Fenpiclonil.

The oxazolidinone compound may, for example, be Famoxadone.

The thiazole carboxamide compound may, for example, be Ethaboxam.

The silyl amide compound may, for example, be Silthiopham.

The aminoacid amidecarbamate compound may, for example, be Iprovalicarb or Benthiavalicarb.

The imidazolidine compound may, for example, be Fenamidone.

The hydroxyanilide compound may, for example, be Fenhexamid.

The benzene sulfonamide compound may, for example, be Flusulfamid.

The oxime ether compound may, for example, be Cyflufenamid.

The phenoxyamide compound may, for example, be Fenoxanil.

The benzophenone compound may, for example, be Metrafenone. Metrafenone is a compound disclosed in AG CHEM NEW COMPOUND REVIEW, VOLUME 21, 2003, p. 17.

Another compound may, for example, be Isoprothiolane, Pyroquilon, Diclomezine, Quinoxyfen, Propamocarb Hydrochloride, Chloropicrin, Dazomet, Metam-sodium, Nicobifen, Diclocymet or Proquinazid.

The fungicide (b) as an active ingredient in the fungicidal composition of the present invention may be the above-mentioned compounds. Among them, it is preferred to use at least one member selected from the group consisting of the strobilurin compound, the azole compound, the morpholine compound, the pyrimidinamine compound, the guanidine compound, the organic chlorine compound, the imidazole compound, the antibiotic, the piperidine compound and the benzophenone compound. It is more preferred to use at least one member selected from the group consisting of Kresoxim-Methyl, Azoxystrobin, Epoxiconazole, Triflumizole, Oxpoconazole fumarate, Tebuconazole, Imibenconazole, Tetraconazole, Cyproconazole, Metconazole, Fluquinconazole, Triadimenol, Fenpropimorph, Spiroxamine, Mepanipyrim, Iminoctadine, Chlorothalonil, Cyazofamid, Polyoxins, Fenpropidine and Metrafenone.

Effects of the Invention

The fungicidal composition of the present invention has stable and high fungicidal effects against cultivated crops infected with plant diseases, and it is possible to control the plant diseases by this composition.

BEST MODE FOR CARRYING OUT THE INVENTION

Preferred processes for production of the compound of the above formula (I) or its salt will be exemplified below.

(1) A process for producing a compound of the above formula (I) or its salt by reacting a substituted benzaldehyde represented by the formula (VI-1):

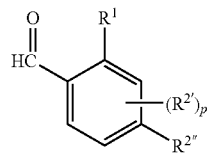

(wherein $R^1$, $R^{2'}$, $R^{2''}$ and p are as defined above) with a metal salt of a substituted pyridine derivative represented by the formula (VII-1):

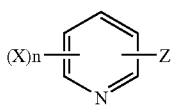

(wherein X is as defined above, and Z is a metal atom or its complex salt) to produce phenylpyridylmethanol represented by the formula (X):

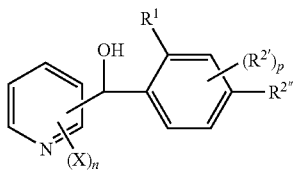

(wherein X, $R^1$, $R^{2'}$, $R^{2''}$, n and p are as defined above), and oxidizing it.

(2) A process for producing a compound of the above formula (I) or its salt by reacting a metal salt of a substituted benzene derivative represented by the formula (VI-2):

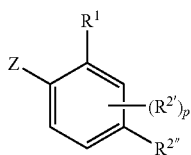

(wherein $R^1$, $R^{2'}$, $R^{2''}$ and p are as defined above, and Z is a metal atom or its complex salt) with a substituted pyridylaldehyde represented by the formula (VII-2):

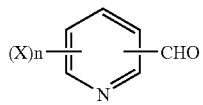

(wherein X and n are as defined above) to produce phenylpyridylmethanol represented by the formula (X), and oxidizing it.

In the above Production Processes (1) and (2), the metal atom represented by Z may, for example, be a typical metal atom such as lithium, magnesium, zinc or copper; or a transition metal atom such as palladium or ruthenium. Further, it may be a composite salt of a metal atom (ate complex) such as lithium diaryl cuprate or lithium triaryl cuprate instead of the metal atom.

The compounds of the above formulae (VI-1) and (VII-2) can be produced usually in accordance with a known method such as a method disclosed in Journal of Organic Chemistry, vol. 57, p. 6,847 to 6,852, 1992.

The phenylpyridylmethanol represented by the formula (X) to be produced by the above Production Processes (1) and (2) is oxidized by known procedures such as a metal oxidizing agent such as manganese dioxide or chromic acid, swern oxidation method (dimethyl sulfoxide and oxalyl chloride) or ruthenium oxidation method (tetrapropylammonium perruthenate and N-methyl morpholine-N-oxide) and converted into the compound represented by the formula (I).

The compound of the formula (VII-1) in Production Process (1) can be obtained by reacting a compound represented by the formula (VIII):

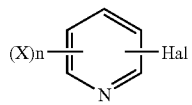

(wherein X and n are as defined above, and Hal is a halogen atom) with a compound represented by the formula (IX): Ar—Z (wherein Ar is an alkyl group or an aryl group, and Z is as defined above). This reaction is carried out preferably in the presence of a solvent at a reaction temperature of from −100° C. to 120° C. Further, Ar—Z may, for example, be isopropylmagnesium chloride, isopropylmagnesium bromide, methyllithium, butyllithium, phenyllithium or diisopropylmagnesium. Otherwise, it may be obtained by a hydrogen-metal exchange reaction using a metal amide such as lithium diisopropylamide or lithium 2,2,6,6-tetramethylpiperazide.

(3) A process for producing a compound of the above formula (I) or its salt by reacting a compound of the above formula (VIII) with a compound represented by the formula (XI):

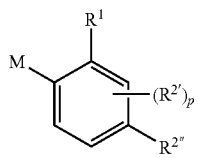

(wherein $R^1$, $R^{2'}$, $R^{2''}$ and p are as defined above, and M is a metal atom) in the presence of a transition metal catalyst under carbon monoxide atmosphere.

In the above Production Process (3), the metal atom may, for example, be hydroxyboron, alkylboron, alkoxyboron, magnesium halide, zinc halide, alkyltin, alkylsilane or alkoxysilane. Further, the transition metal catalyst may, for example, be palladium, rhodium or ruthenium. This reaction is carried out preferably in the presence of a single or mixed inert solvent at a reaction temperature of from 0° C. to 200° C. Further, this reaction must be carried out in a carbon monoxide atmosphere under normal pressure or under a pressurized state by carbon monoxide using a pressure resistant reaction apparatus.

(4) A process for producing a compound of the above formula (I) or its salt by reacting a compound of the above formula (VII-1) with a compound represented by the formula (XII):

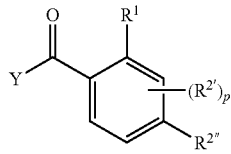

(wherein $R^1$, $R^{2'}$, $R^{2''}$ and p are as defined above, and Y is a leaving group).

In the above Production Process (4), the leaving group represented by Y may, for example, be halogen, cyano or alkoxy. This reaction is carried out preferably in the presence of a single or mixed inert solvent selected from aliphatic hydrocarbons such as hexane, cyclohexane and octane; and ether solvents such as diisopropyl ether, tetrahydrofuran and dimethoxyethane at a reaction temperature of from −100° C. to 120° C. Further, it is possible to accelerate the reaction by using a transition metal complex of e.g. nickel, palladium or iron as a catalyst.

(5) A process for producing a compound of the above formula (I) or its salt by reacting a compound represented by the formula (XIII):

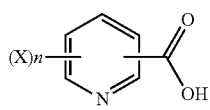

(wherein X and n are as defined above) with a compound is represented by the formula (XIV):

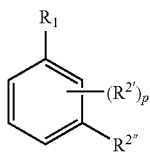

(wherein $R^1$, $R^{2'}$, $R^{2''}$ and p are as defined above) in the presence of a Lewis acid or a dehydrating agent.

The reaction in Production Process (5) is carried out preferably in the presence of a solvent at a reaction temperature of from 0° C. to 200° C. The Lewis acid or the dehydrating agent may, for example, be $P_2O_5$, phosphorus oxychloride, polyphosphoric acid, sulfuric acid or dicyclohexylcarbodiimide (DCC). Further, the solvent may be any solvent so long as it is not involved in the reaction, and it may, for example, be a halogenated hydrocarbon such as 1,2-dichloroethane or methylene chloride, an aromatic hydrocarbon such as benzene, chlorobenzene, dichlorobenzene or nitrobenzene, or a mixture thereof.

(6) A process for producing a compound of the above formula (I) or its salt, comprising a first step (a) of reacting a compound of the above formula (XIII) with a halogenating agent to obtain a compound represented by the formula (XV):

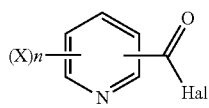

(wherein X and n are as define above, and Hal is a halogen atom) and a second step (b) of subjecting the compound of the formula (XV) obtained in the first step and a compound of the above formula (XIV) to Friedel-Crafts reaction to obtain the compound of the above formula (I).

To the reaction in the first step of Production Process (6), a usual acid halogenating reaction may be applied. This reaction is carried out preferably in the presence or absence of an inert solvent at a reaction temperature of from 0 to 200° C. The halogenating agent to be used in this reaction may, for example, be a fluorinating agent, a chlorinating agent or a brominating agent, and it is preferably a chlorinating agent such as thionyl chloride, phosphorus oxychloride or oxalyl chloride. The Friedel-Crafts reaction in the second step of Production Process (6) may be carried out in the presence of a catalyst in a solvent or without solvent at a reaction temperature of from −78° C. to 200° C., and it is carried out preferably at a reaction temperature of from 0° C. to 100° C. The catalyst to be used in the reaction may, for example, be a Lewis acid catalyst such as $FeCl_3$, $AlCl_3$, $SnCl_4$, $ZnCl_2$, $TiCl_4$, $SbCl_5$, $BF_3$ or $BiCl_3$, trifluoromethanesulfonic acid or graphite. Further, the solvent is an inert solvent under reaction conditions and it may, for example, be 1,2-dichloroethane, methylene chloride, chlorobenzene, dichlorobenzene or nitrobenzene, or a mixture thereof. Further, the product may be produced by synthesis or derivatizing with reference to Friedel-Crafts Chemistry (Olah, G. A.).

The compound of the above formula (XIII) to be used as a starting material for production in Production Processes (5) and (6) may be obtained by oxidizing a compound of the above formula (VII-2). The oxidizing agent may be an inorganic or organic oxidizing agent which is commonly used. Otherwise, it may be obtained by reacting a compound of the above formula (VII-1) directly with dry ice or by reacting it with ethyl chlorocarbonate, followed by hydrolysis. Otherwise, the product may be produced by synthesis or derivatizing from a substituted pyridinecarboxylic acid or its derivative by a known method from literature, e.g. with reference to J. Heterocyclic. Chem., 36, 653 (1999). Further, the product may be produced by synthesis or derivatizing with reference to "Experimental Chemistry 22, Organic Syntheses IV, 1992", fourth edition, The Chemical Society of Japan.

Among benzoylpyridine derivatives represented by the formula (I), preferred is a compound represented by the formula (I'):

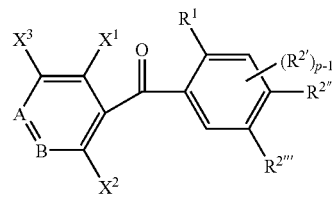

(wherein when A is —N═, B is —$CX^4$═; when A is —CH═, B is —N═; each of $X^1$ and $X^2$ which are independent of each other, is a halogen atom, an alkoxy group, a hydroxyl group, an alkyl group, a $CF_3$ group or an alkylthio group; $X^3$ is a hydrogen atom, a halogen atom, an alkoxy group, an alkyl group, a $CF_3$ group or an alkylthio group; $X^4$ is a hydrogen atom, a halogen atom, an alkoxy group, an alkyl group, a $CF_3$ group or an alkylthio group; $R^1$ is an alkyl group; $R^{2'}$ is an alkoxy group; p is 1, 2 or 3; and each of $R^{2''}$ and $R^{2'''}$ is an alkoxy group).

The compound represented by the above formula (I') may be a compound wherein A is —CH═ and B is —N═ i.e. a compound represented by the formula (I'-1):

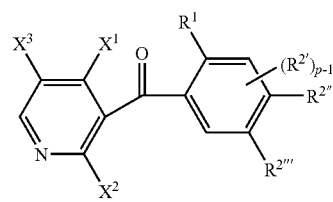

(wherein $X^1$, $X^2$, $X^3$, $R^1$, $R^{2'}$, $R^{2''}$ and $R^{2'''}$ are as defined above), and a compound wherein A is —N= and B is —$CX^4$= i.e. a compound represented by the formula (I'-2):

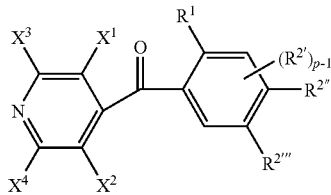

(wherein $X^1$, $X^2$, $X^3$, $X^4$, $R^1$, $R^{2'}$, $R^{2''}$ and $R^{2'''}$ are as defined above).

Among compounds represented by the above formula (I'-1), it is preferred to use at least one compound selected from the group consisting of 3-(2,3,4-trimethoxy-6-methylbenzoyl)-4-bromo-5-chloro-2-methoxypyridine (Compound No. 1), 3-(2,3,4-trimethoxy-6-methylbenzoyl)-5-chloro-4-ethyl-2-methoxypyridine (Compound No. 2), 3-(4,5-dimethoxy-2-methylbenzoyl)-4,5-dichloro-2-methoxypyridine (Compound No. 3), 3-(5-ethoxy-4-methoxy-2-methylbenzoyl)-4,5-dichloro-2-methoxypyridine (Compound No. 4), 3-(2,3,4-trimethoxy-6-methylbenzoyl)-4-bromo-5-chloro-2-ethoxypyridine (Compound No. 5), 3-(2,3,4-trimethoxy-6-methylbenzoyl)-5-chloro-2-ethoxy-4-methylpyridine (Compound No. 6), 3-(2,3,4-trimethoxy-6-methylbenzoyl)-5-bromo-4-chloro-2-ethoxypyridine (Compound No. 7), 3-(2,3,4-trimethoxy-6-methylbenzoyl)-4-chloro-5-iodo-2-methoxypyridine (Compound No. 8), 3-(2,3,4-trimethoxy-6-methylbenzoyl)-5-iodo-2,4-dimethoxypyridine (Compound No. 9), 3-(2,3,4-trimethoxy-6-methylbenzoyl)-5-chloro-2-methoxy-4-methylthiopyridine (Compound No. 10), 3-(2,3,4-trimethoxy-6-methylbenzoyl)-5-chloro-2,4-dimethoxypyridine (Compound No. 11), 3-(2,3,4-trimethoxy-6-methylbenzoyl)-4,5-dibromo-2-methoxypyridine (Compound No. 12), 3-(2,3,4-trimethoxy-6-methylbenzoyl)-4-bromo-2-methoxy-5-methylpyridine (Compound No. 13), 3-(2,3,4-trimethoxy-6-methylbenzoyl)-5-bromo-4-trifluoromethyl-2-methoxypyridine (Compound No. 14), 3-(2,3,4-trimethoxy-6-methylbenzoyl)-4,5-dichloro-2-methoxypyridine (Compound No. 15), 3-(2,3,4-trimethoxy-6-methylbenzoyl)-2,4-dichloro-5-methylpyridine (Compound No. 16), 3-(2,3,4-trimethoxy-6-methylbenzoyl)-2,4-dichloro-5-iodopyridine (Compound No. 17), 3-(2,3,4-trimethoxy-6-methylbenzoyl)-2-fluoro-4-iodo-5-methylpyridine (Compound No. 18), 3-(2,3,4-trimethoxy-6-methylbenzoyl)-2-fluoro-4,5-dimethylpyridine (Compound No. 19), 3-(2,3,4-trimethoxy-6-methylbenzoyl)-2-methoxy-4,5-dimethylpyridine (Compounds No. 20), 3-(2-ethoxy-3,4-dimethoxy-6-methylbenzoyl)-2-ethoxy-4,5-dimethylpyridine (Compound No. 21), 3-(2,3,4-trimethoxy-6-methylbenzoyl)-4,5-dimethyl-2-methylthiopyridine (Compound No. 22), 3-(2,3,4-trimethoxy-6-methylbenzoyl)-5-bromo-4-chloro-2-methoxypyridine (Compound No. 23), 3-(2,3,4-trimethoxy-6-methylbenzoyl)-4-chloro-2-methoxy-5-methylpyridine (Compound No. 24), 3-(2,3,4-trimethoxy-6-methylbenzoyl)-2-chloro-5-trifluoromethyl-4-methylpyridine (Compound No. 25), 3-(2,3,4-trimethoxy-6-methylbenzoyl)-5-trifluoromethyl-2-methoxy-4-methylpyridine (Compound No. 26), 3-(2,3,4-trimethoxy-6-methylbenzoyl)-2,4-dichloro-5-trifluoromethylpyridine (Compound No. 27), 3-(2,3,4-trimethoxy-6-methylbenzoyl)-4-chloro-5-trifluoromethyl-2-methoxypyridine (Compound No. 28), 3-(2,3,4-trimethoxy-6-methylbenzoyl)-5-chloro-4-ethynyl-2-methoxypyridine (Compound No. 29), 3-(2,3,4-trimethoxy-6-methylbenzoyl)-5-chloro-4-fluoromethyl-2-methoxypyridine (Compound No. 30), 3-(2,3,4-trimethoxy-6-methylbenzoyl)-5-bromo-4-fluoromethyl-2-methoxypyridine (Compound No. 31), 3-(2,3,4-trimethoxy-6-methylbenzoyl)-4-fluoromethyl-2-methoxy-5-methylpyridine (Compound No. 32), 3-(2,3,4-trimethoxy-6-methylbenzoyl)-5-chloro-4-difluoromethyl-2-methoxypyridine (Compound No. 33), 3-(2,3,4-trimethoxy-6-methylbenzoyl)-5-ethyl-4-trifluoromethyl-2-methoxypyridine (Compound No. 34), 3-(2,3,4-trimethoxy-6-methylbenzoyl)-5-chloro-2-methoxy-4-methylpyridine (Compound No. 35), 3-(2,3,4-trimethoxy-6-methylbenzoyl)-5-bromo-2-methoxy-4-methylpyridine (Compound No. 36), 3-(2,3,4-trimethoxy-6-methylbenzoyl)-4-trifluoromethyl-2-methoxy-5-methylpyridine (Compound No. 37) and 3-(4,5-dimethoxy-2-methylbenzoyl)-5-chloro-2-methoxy-4-methylpyridine (Compound No. 38).

Among compounds represented by the above formula (I'-2), it is preferred to use at least one compound selected from the group consisting of 4-(2,3,4-trimethoxy-6-methylbenzoyl)-2,5-dichloro-3-trifluoromethylpyridine (Compound No. 39), 4-(2,3,4-trimethoxy-6-methylbenzoyl)-2-chloro-3-trifluoromethyl-5-methoxypyridine (Compound No. 40), 4-(2,3,4-trimethoxy-6-methylbenzoyl)-2-bromo-3-trifluoromethyl-5-methoxypyridine (Compound No. 41), 4-(2,3,4-trimethoxy-6-methylbenzoyl)-2,3,5-trichloropyridine (Compound No. 42), 4-(2,3,4-trimethoxy-6-methylbenzoyl)-3,5-dichloropyridine (Compound No. 43), 4-(2,3,4-trimethoxy-6-methylbenzoyl)-3-chloro-5-methoxypyridine (Compound No. 44), 4-(2,3,4-trimethoxy-6-methylbenzoyl)-2-bromo-3-chloro-5-methoxypyridine (Compound No. 45) and 4-(2,3,4-trimethoxy-6-methylbenzoyl)-3-bromo-5-methylpyridine (Compound No. 46).

The fungicidal composition of the present invention is useful particularly as an agricultural and horticultural fungicide. As the agricultural and horticultural fungicide, it is effective for controlling diseases such as blast, brown spot or sheath blight of rice (*Oryza sativa*, etc.); powdery mildew, scab, rust, snow mold, snow blight, loose smut, eye spot, leaf spot or glume blotch of cereals (*Hordeum vulgare, Tricum aestivum*, etc.); melanose or scab of citrus (*Citrus* spp., etc.); blossom blight, powdery mildew, *Alternaria* leaf spot or scab of apple (*Malus pumila*); scab or black spot of pear (*Pyrus serotina, Pyrus ussuriensis, Pyrus communis*); brown rot, scab or *Phomopsis* rot of peach (*Prunus persica*, etc.); anthracnose, ripe rot, powdery mildew or downy mildew of grape (*Vitis vinifera* spp., etc.); anthracnose or brown stem rot of Japanese persimmon (*Diospyros kaki*, etc.); anthracnose, powdery mildew, gummy stem blight or downy mildew of cucurbit (*Cucumis melo*, etc.); early blight, leaf mold or late blight of tomato (*Lycopersicon esculentum*); various *Alternaria* disease pathogens of cruciferous vegetables (*Brassica* sp., *Raphanus* sp., etc); late blight or early blight of potato (*Solanum tuberosum*); powdery mildew of strawberry (*Fragaria*, etc.); and gray mold or disease caused by *Sclerotinia* of various crops. It is particularly effective against powdery mildew of cereals and vegetables and blast of rice. Further, it is effective also for controlling soil diseases caused by plant pathogens such as *Fusarium, Pythium, Rhizoctonia, Verticillium* and *Plasmodiophora*.

The plurality of the active ingredients constituting the fungicidal composition of the present invention are, in the same manner as conventional agricultural chemicals, mixed with various adjuvants and formulated into various formulations such as a dust, granules, water-dispersible granules, a wettable powder, a water-based suspension concentrate, an oil-based suspension concentrate, water soluble granules, an emulsifiable concentrate, a soluble concentrate, a paste, an aerosol and an ultra low-volume formulation. However, so long as the purpose of the present invention can be accomplished, any type of formulation which is commonly used in this field is applicable. Such adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethyl sulfoxide, dimethylformamide, dimethylacetamide, N-methyl-2-pyrrolidone and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected from known components so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed. The blend ratio of the active ingredient components to the various adjuvants is usually from 0.005:99.995 to 95:5, preferably from 0.2:99.8 to 90:10. In the actual application of such a formulation, it may be used as it is, or may be diluted to a predetermined concentration with a diluent such as water, and various spreaders may be added thereto, as the case requires.

A method for controlling plant diseases, which comprises applying the fungicidal composition of the present invention to agricultural and horticultural plants, is also included in the present invention. The concentration of the fungicidal composition of the present invention can not generally be defined, as it varies depending upon the crop plants to be treated, the application method, the type of the formulation, the dose, etc. However, it is applied in a concentration of the active ingredients being usually from 0.1 to 10,000 ppm, preferably from 1 to 2,000 ppm in the case of foliage treatment, and usually from 10 to 100,000 g/ha, preferably from 200 to 20,000 g/ha in the case of soil treatment.

The formulation containing the fungicidal composition of the present invention or a diluted product thereof may be applied by an application method which is commonly used, such as spreading (spreading, spraying, misting, atomizing, grain diffusing or application on water surface), soil application (such as mixing or irrigation) or surface application (such as coating, dust coating or covering). Further, it may be applied also by so-called ultra low volume. In this method, the formulation may contain 100% of the active ingredient.

In the fungicidal composition of the present invention, the appropriate mixing weight ratio of the benzoylpyridine derivative represented by the formula (I) or its salt to another fungicide is usually from 1:10,000 to 10,000:1, preferably from 1:1,000 to 1,000:1, more preferably from 1:200 to 200:1.

EXAMPLES

Now, the present invention will be described in further detail with reference to Examples. However, it should be understood that the present invention is by no means restricted thereto.

Preparation Example 1

Preparation of 3-(2,3,4-trimethoxy-6-methylbenzoyl)-4,5-dichloro-2-methoxypyridine (Compound No. 15)

(a) 222 ml of n-butyllithium (1.57 mo/l hexane solution) was dropwise added at −20° C. to a solution having 34.2 g (340 mmol) of diisopropylamine dissolved in 400 ml of tetrahydrofuran, followed by stirring for 1 hour. The solution was cooled to −78° C., and a solution having 32.0 g (330 mmol) of 2-fluoropyridine dissolved in 50 ml of tetrahydrofuran was added, followed by stirring for 4 hours to prepare 2-fluoro-3-pyridyllithium. Then, to this solution, a solution having 87.1 g (341 mmol) of iodine dissolved in 150 ml of tetrahydrofuran was added, followed by stirring for 1 hour. 200 ml of water was added to the mixture to terminate the reaction, and tetrahydrofuran was distilled off under reduced pressure. After extraction with ethyl ether, the organic layer was dried over sodium sulfate and subjected to filtration, and the solvent was distilled off under reduced pressure to obtain 67.4 g (crude yield: 92%) of crude 2-fluoro-3-iodopyridine.

$^1$H-NMR (CDCl$_3$, 400 MHz): δ (ppm)=6.91-6.88 (m, 1H), 8.08-8.12 (m, 2H)

(b) 189 ml of n-butyllithium (1.57 mol/l hexane solution) was dropwise added at −20° C. to a solution having 30.2 g (302 mmol) of diisopropylamine dissolved in 380 ml of tetrahydrofuran, followed by stirring for 1 hour. The solution was cooled to −78° C., and a solution having 67.4 g (302 mmol) of crude 2-fluoro-3-iodopyridine obtained in Step (a) dissolved in 100 ml of tetrahydrofuran was added, followed by stirring for 1 hour, so that 2-fluoro-3-iodo-4-pyridyllithium formed at the initial stage was isomerized to 2-fluoro-4-iodo-3-pyridyllithium. 300 ml of water was added to the reaction mixture to terminate the reaction, and tetrahydrofuran was distilled off under reduced pressure. After extraction with ethyl ether, the organic layer was dried over sodium sulfate and subjected to filtration, and the solvent was distilled off under reduced pressure to obtain 59.3 g (crude yield: 89%) of crude 2-fluoro-4-iodopyridine.

$^1$H-NMR (CDCl$_3$, 400 MHz): δ (ppm)=7.33 (d, 1H, J=2.8 Hz), 7.51 (d, 1H, J=5.2 Hz), 7.88 (dd, 1H, J=5.2 Hz, 2.8 Hz)

(c) 500 ml of methanol was added to 59.4 g (253 mmol) of crude 2-fluoro-4-iodopyridine obtained in Step (b) so that it was dissolved in methanol, and 21.5 g (398 mmol) of sodium methoxide was added, followed by reflux with heating for 3 hours. 300 ml of water was added to terminate the reaction, and methanol was distilled off under reduced pressure. After extraction with ethyl ether, the organic layer was dried over sodium sulfate and subjected to filtration, and the solvent was distilled off under reduced pressure to obtain 56.7 g (crude yield: 91%) of crude 4-iodo-2-methoxypyridine.

$^1$H-NMR (CDCl$_3$, 400 MHz): δ (ppm)=3.86 (s, 3H), 7.12-7.16 (m, 2H), 7.79 (d, 1H, J=5.6 Hz)

(d) 50.6 ml (2 mol/l tetrahydrofuran solution) of isopropylmagnesium chloride was cooled with ice, and a solution having 19.8 g (84.3 mmol) of crude 4-iodo-2-methoxypyridine obtained in Step (c) dissolved in 80 ml of tetrahydrofuran was added, followed by stirring at 0° C. for 1 hour and then at room temperature for 1 hour to prepare 2-methoxy-4-pyridylmagnesium chloride. Then, 16.9 g (127 mmol) of N-chlorosuccinimide was gradually added, followed by stirring at room temperature for 1 hour. 100 ml of water was added to terminate the reaction, and tetrahydrofuran was distilled off under reduced pressure. After extraction with ethyl ether, the organic layer was dried over sodium sulfate and subjected to filtration, and the solvent was distilled off under reduced pressure to obtain 11.0 g (crude yield: 91%) of crude 4-chloro-2-methoxypyridine.

$^1$H-NMR (CDCl$_3$, 400 MHz): δ (ppm)=3.91 (s, 3H), 6.70 (d, 1H, J=2.0 Hz), 6.81 (dd, 1H, J=6.0 Hz, 2.0 Hz), 7.99 (d, 1H, J=6.0 Hz)

(e) 10.0 g (69.9 mmol) of crude 4-chloro-2-methoxypyridine obtained in Step (d) was dissolved in 100 ml of dimethylformamide, and 37.2 g (279 mmol) of N-chlorosuccinimide was added, followed by stirring at room temperature for 12 hours. 400 ml of water was added to terminate the reaction, followed by extraction with ethyl ether. The organic layer was washed with a saturated sodium chloride solution, dried over sodium sulfate and subjected to filtration, and the solvent was distilled off under reduced pressure to obtain 9.10 g (crude yield: 73%) of crude 4,5-dichloro-2-methoxypyridine.

$^1$H-NMR (CDCl$_3$, 400 MHz): δ (ppm)=3.90 (s, 3H), 6.85 (s, 1H), 8.14 (s, 1H)

(f) 15.1 ml of n-butyllithium (1.57 mol/l hexane solution) was dropwise added at −20° C. to a solution having 2.40 g (23.7 mmol) of diisopropylamine dissolved in 30 ml of tetrahydrofuran, followed by stirring for 1 hour. The solution was cooled to −78° C., and a solution having 4.22 g (23.6 mmol) of 4,5-dichloro-2-methoxypyridine obtained in Step (e) dissolved in 20 ml of tetrahydrofuran was added, followed by stirring for 2 hours to prepare 4,5-dichloro-2-methoxy-3-pyridyllithium. Then, to this solution, a solution having 5.00 g (23.8 mmol) of 2,3,4-trimethoxy-6-methylbenzaldehyde dissolved in 20 ml of tetrahydrofuran was added, followed by stirring for 30 minutes. 50 ml of water was added to the mixture to terminate the reaction, and tetrahydrofuran was distilled off under reduced pressure. After extraction with ethyl ether, the organic layer was dried over sodium sulfate and subjected to filtration, and the solvent was distilled off under reduced pressure, followed by purification by silica gel column chromatography to obtain 4.66 g (yield: 51%) of (2,3,4-trimethoxy-6-methylphenyl)(4,5-dichloro-2-methoxy-3-pyridyl)methanol.

$^1$H-NMR (CDCl$_3$, 400 MHz): δ (ppm)=2.32 (s, 3H), 3.52 (s, 3H), 3.77 (s, 3H), 3.82 (s, 3H), 4.11 (s, 3H), 5.32 (d, 1H, J=10.0 Hz), 6.21 (d, 1H, J=10.0 Hz), 6.55 (s, 1H), 8.07 (s, 1H)

(g) 13.8 g (159 mmol) of manganese dioxide was added to a solution having 4.66 g (12.0 mmol) of (2,3,4-trimethoxy-6-methylphenyl)(4,5-dichloro-2-methoxy-3-pyridyl)methanol obtained in Step (f) dissolved in 30 ml of toluene, followed by reflux with heating for 2 hours. After cooling to room temperature, manganese dioxide was removed by filtration on the pad of celite, and toluene was distilled off under reduced pressure, followed by purification by silica gel column chromatography to obtain 2.98 g (yield: 65%) of 3-(2,3,4-trimethoxy-6-methylbenzoyl)-4,5-dichloro-2-methoxypyridine.

$^1$H-NMR (CDCl$_3$, 400 MHz) δ (ppm)=2.46 (s, 3H), 3.45 (s, 3H) 3.74 (s, 3H), 3.90 (s, 3H), 4.00 (s, 3H), 6.55 (s, 1H), 8.13 (s, 1H)

Preparation Example 2

Preparation of 3-(2,3,4-trimethoxy-6-methylbenzoyl)-2-methoxy-4,5-dimethylpyridine (Compound No. 20)

(a) 26.5 ml of n-butyllithium (1.57 mol/l hexane solution) was dropwise added at −78° C. to a solution having 4.02 g (39.8 mmol) of diisopropylamine dissolved in 70 ml of tetrahydrofuran, followed by stirring for 30 minutes. To this solution, a solution having 4.42 g (39.8 mmol) of 2-fluoro-5-methylpyridine dissolved in 18 ml of tetrahydrofuran was added, followed by stirring for 4 hours to prepare 2-fluoro-5-methyl-3-pyridyllithium. Then, to this solution, a solution having 10.1 g (39.8 mmol) of iodine dissolved in 27 ml of tetrahydrofuran was added, followed by stirring for 2 hours. 16 ml of water and 120 ml of a sodium thiosulfate aqueous solution were charged, followed by extraction with ethyl ether. The organic layer was dried over magnesium sulfate and subjected to filtration, the solvent was distilled off under reduced pressure, and the obtained crude product was purified by silica gel chromatography to obtain 3.15 g (yield: 33%) of 2-fluoro-3-iodo-5-methylpyridine.

$^1$H-NMR (CDCl$_3$, 400 MHz): δ (ppm)=2.27 (s, 3H), 7.95 (m, 2H)

(b) 8.90 ml (1.57 mol/l hexane solution) was dropwise added at −78° C. to a solution having 1.34 g (13.3 mmol) of diisopropylamine dissolved in 27 ml of tetrahydrofuran, followed by stirring for 30 minutes. To this solution, a solution having 3.15 g (13.3 mmol) of 2-fluoro-3-iodo-5-methylpyridine obtained in Step (a) dissolved in 5 ml of tetrahydrofuran was added, followed by stirring for 1 hour, so that 2-fluoro-3-iodo-5-methyl-4-pyridyllithium formed at the initial stage was isomerized to 2-fluoro-4-iodo-5-methyl-3-pyridyllithium. To the reaction mixture, a solution having 2.79 g (13.3 mmol) of 2,3,4-trimethoxy-6-methylbenzaldehyde dissolved in 5 ml of tetrahydrofuran was added, followed by stirring for 2 hours. After the temperature was increased to room temperature, 50 ml of water was added, followed by extraction with ethyl ether. The organic layer was dried over magnesium sulfate and subjected to filtration, the solvent was distilled off under reduced pressure, and the obtained crude product was purified by silica gel chromatography to obtain 4.45 g (yield: 75%) of (2,3,4-trimethoxy-6-methylphenyl)(2-fluoro-4-iodo-5-methyl-3-pyridyl)methanol.

$^1$H-NMR (CDCl$_3$, 400 MHz): δ (ppm)=2.21 (s, 3H), 2.42 (s, 3H), 3.72 (s, 3H), 3.79 (s, 3H), 3.81 (s, 3H), 4.97 (d, 1H, J=10.0 Hz), 6.08 (d, 1H, J=10.0 Hz), 6.46 (s, 1H), 7.86 (s, 1H)

(c) 17.3 g (0.18 mol) of manganese dioxide was added to a solution having 4.35 g (9.70 mmol) of (2,3,4-trimethoxy-6-methylphenyl)(2-fluoro-4-iodo-5-methyl-3-pyridyl)methanol obtained in Step (b) dissolved in 130 ml of toluene, followed by reflux with heating for 2 hours. After cooling to room temperature, manganese dioxide was removed by filtration on the pad of celite, and toluene was distilled off under reduced pressure, followed by purification by silica gel chromatography to obtain 2.80 g (yield: 65%) of 3-(2,3,4-trimethoxy-6-methylbenzoyl)-2-fluoro-4-iodo-5-methylpyridine (Compound No. 18, melting point 140 to 141° C.).

$^1$H-NMR (CDCl$_3$, 400 MHz): δ (ppm)=2.41 (s, 3H), 2.50 (s, 3H), 3.42 (s, 3H), 3.90 (s, 3H), 3.74 (s, 3H), 6.57 (s, 1H), 7.94 (s, 1H)

(d) 1.50 g (3.37 mmol) of 3-(2,3,4-trimethoxy-6-methylbenzoyl)-2-fluoro-4-iodo-5-methylpyridine obtained in Step (c), 1.40 g (10.1 mmol) of potassium carbonate, 0.39 g (0.34 mmol) of tetrakis(triphenylphosphine)palladium, 15 ml of dioxane and 0.42 g (1.67 mmol) of 50% trimethylboroxin were mixed, followed by reflux with heating for 6 hours. After cooling to room temperature, filtration on the pad of celite and washing with ethyl acetate and tetrahydrofuran were carried out, the solvent was distilled off under reduced pressure, and the obtained crude product was purified by silica gel chromatography to obtain 0.79 g (yield: 70%) of 3-(2,3,4-trimethoxy-6-methylbenzoyl)-2-fluoro-4,5-dimethylpyridine (Compound No. 19).

$^1$H-NMR (CDCl$_3$, 400 MHz): δ (ppm)=2.28 (s, 3H), 2.32 (s, 3H), 2.42 (s, 3H), 3.35 (s, 3H), 3.74 (s, 3H), 3.90 (s, 3H), 6.57 (s, 1H), 7.94 (s, 1H)

(e) A solution having 0.06 g (1.5 mmol) of 60% sodium hydride dissolved in 1 ml of methanol, was dropwise added to a solution having 0.20 g (0.60 mmol) of 3-(2,3,4-trimethoxy-6-methylbenzoyl)-2-fluoro-4,5-dimethylpyridine obtained in Step (d) dissolved in 2.5 ml of methanol, followed by reflux with heating for 16 hours. After cooling to room temperature, 5 ml of water was added, and diluted hydrochloric acid was added to bring the solution weakly acidic. After extraction with ethyl ether, washing with a sodium chloride solution was carried out, and the organic layer was dried over magnesium sulfate and subjected to filtration, the solvent was distilled off under reduced pressure, and the obtained crude product was purified by silica gel chromatography to obtain 89.0 mg (yield: 43%) of 3-(2,3,4-trimethoxy-6-methylbenzoyl)-2-methoxy-4,5-dimethylpyridine.

$^1$H-NMR (CDCl$_3$, 400 MHz): δ (ppm)=2.19 (s, 3H), 2.21 (s, 3H), 2.39 (s, 3H), 3.24 (s, 3H), 3.70 (s, 3H), 3.74 (s, 3H), 3.87 (s, 3H), 6.53 (s, 1H), 7.87 (s, 1H)

Preparation Example 3

Preparation of 3-(2,3,4-trimethoxy-6-methylbenzoyl)-5-bromo-4-chloro-2-methoxypyridine (Compound No. 23)

(a) 5.76 g (40.1 mmol) of 4-chloro-2-methoxypyridine was dissolved in 20 ml of dimethylformamide, and a dimethylformamide (20 ml) solution of 8.01 g of N-bromosuccinimide (98%, 44.1 mmol) was dropwise added over a period of 30 minutes. After stirring at room temperature for 2 days, an unreacted material was confirmed, and thus 2.85 g of N-bromosuccinimide (98%, 16 mmol) was further added, followed by stirring at room temperature further for 3 days. The reaction mixture was poured into 250 ml of water, followed by extraction with ethyl ether (100 ml each) three times. The organic layer was washed with water (100 ml), a sodium thiosulfate aqueous solution (100 ml) and then a saturated sodium chloride solution (100 ml), dried over magnesium sulfate and subjected to filtration, and the solvent was distilled off under reduced pressure. The obtained crude product was purified by silica gel chromatography to obtain 7.10 g (yield: 30%) of 5-bromo-4-chloro-2-methoxypyridine.

$^1$H-NMR (CDCl$_3$, 400 MHz): δ (ppm)=3.91 (s, 3H), 6.89 (s, 1H), 8.28 (s, 1H)

(b) 18.3 ml of n-butyllithium (1.57 mol/l hexane solution, 27 mmol) was dropwise added at 0° C. to a solution having 3.84 g (27 mmol) of 2,2,6,6-tetramethylpiperidine dissolved in 36 ml of tetrahydrofuran under an argon stream, followed by stirring at 0° C. for 30 minutes. The obtained solution was cooled to −78° C., and a solution having 6.10 g (27 mmol) of 5-bromo-4-chloro-2-methoxypyridine dissolved in 24 ml of tetrahydrofuran was added, followed by stirring at the same temperature for 2 hours to prepare 5-bromo-4-chloro-2-methoxy-3-pyridyllithium. Then, a solution having 5.50 g (26 mmol) of 2,3,4-trimethoxy-6-methylbenzaldehyde dissolved in 24 ml of tetrahydrofuran was added, followed by stirring at the same temperature for 1 hour. To the reaction mixture, 37 ml of a saturated ammonium chloride aqueous solution and then 150 ml of water were added, and the temperature was increased to room temperature, followed by extraction with ethyl acetate (150 ml each) three times. The organic layer was washed with a saturated sodium chloride solution (100 ml), dried over magnesium sulfate and subjected to filtration, and the solvent was distilled off under reduced pressure. The obtained crude product was purified by silica gel chromatography to obtain 6.53 g (yield: 56%) of (2,3,4-trimethoxy-6-methylphenyl)(5-bromo-4-chloro-2-methoxy-3-pyridyl)methanol.

$^1$H-NMR (CDCl$_3$, 400 MHz): δ (ppm)=2.33 (s, 3H), 3.54 (s, 3H) 3.79 (s, 3H), 3.84 (s, 3H), 3.98 (s, 3H), 5.32 (d, 1H J=9.6 Hz), 6.23 (d, 1H J=9.6 Hz), 6.49 (s, 1H), 8.21 (s, 1H)

4.55 g of manganese dioxide (88%, 46 mmol) was added to a solution having 2.21 g (5.1 mmol) of (2,3,4-trimethoxy-6-methylphenyl)(5-bromo-4-chloro-2-methoxy-3-pyridyl) methanol dissolved in 70 ml of toluene, followed by reflux with heating for 1 hour. 4.55 g of manganese dioxide (88%, 46 mmol) was further added, followed by reflux with heating for 1 hours. The reaction mixture was cooled to room temperature, manganese dioxide was removed by filtration on the pad of celite, and toluene was distilled off under reduced pressure. The obtained crude product was purified by silica gel chromatography to obtain 1.90 g (yield: 87%) of 3-(2,3,4-trimethoxy-6-methylbenzoyl)-5-bromo-4-chloro-2-methoxypyridine (melting point 84 to 87° C.).

$^1$H-NMR (CDCl$_3$, 400 MHz): δ (ppm)=2.48 (s, 3H), 3.45 (s, 3H) 3.75 (s, 3H), 3.87 (s, 3H), 3.91 (s, 3H), 6.57 (s, 1H), 8.27 (s, 1H)

Preparation Example 4

Preparation of 3-(2,3,4-trimethoxy-6-methylbenzoyl)-5-chloro-2-methoxy-4-methylpyridine (Compound No. 35)

(a) 9.2 g (69 mmol) of N-chlorosuccinimide was charged to a N,N-dimethylformamide (DMF) 15 ml solution of 8.0 g (65 mmol) of 2-methoxy-4-methylpyridine, followed by stirring for 18 hours. Water was added to the reaction solution, and the aqueous layer was extracted with diethyl ether. The organic layer was washed with a saturated sodium chloride solution, dried over anhydrous sodium sulfate and subjected to filtration, and the solvent was distilled off under reduced pressure. The crude product was purified by silica gel column chromatography to obtain 8.5 g (yield: 82%) of 5-chloro-2-methoxy-4-methylpyridine (melting point 32 to 33° C.).

$^1$HNMR (CDCl$_3$, 300 MHz): δ 2.32 (s, 3H), 3.89 (s, 3H), 6.62 (s, 1H), 8.05 (s, 1H)

(b) 20.2 g (114 mmol) of N-bromosuccinimide was charged to a N,N-dimethylformamide (DMF) 15 ml solution of 7.2 g (46 mmol) of 5-chloro-2-methoxy-4-methylpyridine, followed by stirring at 50° C. for 20 hours. A diluted sodium thiosulfate aqueous solution was added to the reaction solution, and the aqueous layer was extracted with diethyl ether. The organic layer was washed with a saturated sodium chloride solution, dried over anhydrous sodium sulfate and subjected to filtration on the pad of a silica gel cake, and the solvent was distilled off under reduced pressure to obtain 10.6 g (yield: 97%) of 3-bromo-5-chloro-2-methoxy-4-methylpyridine (melting point: 44 to 45° C.).

$^1$HNMR (CDCl$_3$, 300 MHz): δ 2.51 (s, 3H), 3.98 (s, 3H), 8.01 (s, 1H)

(c) 4 ml of tetrahydrofuran and 0.62 ml (4.4 mmol) of triethylamine were added to 2.2 ml (4.4 mmol) of isopropylmagnesium chloride (2.0 mol/l tetrahydrofuran solution), the mixture was cooled to 0° C., and a solution having 1.0 g (4.2 mmol) of 3-bromo-5-chloro-2-methoxy-4-methylpyridine dissolved in 5 ml of tetrahydrofuran was dropwise added, followed by stirring for 3 hours to prepare 5-chloro-2-methoxy-4-methyl-3-pyridylmagnesium chloride. A solution having 0.89 g (4.2 mmol) of 2,3,4-trimethoxy-6-methylbenzaldehyde dissolved in 5 ml of tetrahydrofuran was dropwise added to the reaction solution, followed by stirring for 1 hour, and then the temperature was increased to room temperature, followed by stirring further for 1 hour. Water was added to the reaction solution to terminate the reaction, followed by extraction with ethyl acetate. The organic layer was washed with a saturated sodium chloride solution, dried over anhydrous magnesium sulfate and subjected to filtration, and the solvent was distilled off under reduced pressure. The crude product was purified by silica gel column chromatography to obtain 1.1 g (yield: 70%) of (2,3,4-trimethoxy-6-methylphenyl)(5-chloro-2-methoxy-4-methyl-3-pyridyl)methanol (pale yellow oily substance).

$^1$HNMR (CDCl$_3$, 300 MHz): δ 2.26 (s, 3H), 2.27 (s, 3H), 3.54 (s, 3H), 3.80 (s, 3H), 3.84 (s, 3H), 3.94 (s, 3H), 5.32 (d, 1H, J=9.0 Hz), 6.12 (d, 1H, J=9.0 Hz), 6.47 (s, 1H), 8.02 (s, 1H)

(d) 4 g of active manganese dioxide was added to a toluene 15 ml solution of 0.64 g (1.7 mmol) of (2,3,4-trimethoxy-6-methylphenyl)(5-chloro-2-methoxy-4-methyl-3-pyridyl)methanol, followed by stirring under reflux with heating for 1 hour. The reaction solution was subjected to filtration on the pad of celite, and the solvent was distilled off under reduced pressure to obtain 0.57 g (yield: 90%) of 3-(2,3,4-trimethoxy-6-methylbenzoyl)-5-chloro-2-methoxy-4-methylpyridine (melting point 94.5 to 95.5° C.)

$^1$HNMR (CDCl$_3$, 300 MHz): δ 2.31 (s, 3H), 2.40 (s, 3H), 3.30 (s, 3H), 3.73 (s, 3H), 3.74 (s, 3H), 3.88 (s, 3H), 6.54 (s, 1H), 8.06 (s, 1H)

Preparation Example 5

Preparation of 3-(2,3,4-trimethoxy-6-methylbenzoyl)-4-trifluoromethyl-2-methoxy-5-methylpyridine (Compound No. 37)

(a) A solution having 5.05 g (27.8 mmol) of 2-chloro-4-trifluoromethylpyridine and 3.59 g (66.5 mmol) of sodium methoxide dissolved in 40 ml of methanol was stirred under reflux with heating for 4 hours. Water was added to terminate the reaction, followed by extraction with diethyl ether. The organic layer was dried over anhydrous sodium sulfate and subjected to filtration on the pad of a silica gel cake. The solvent was distilled off under reduced pressure to obtain 4.19 g (yield: 85%) of 4-trifluoromethyl-2-methoxypyridine.

$^1$H-NMR (CDCl$_3$, 400 MHz): δ (ppm)=3.96 (s, 3H), 6.95 (s, 1H), 7.05 (d, 1H, J=5.2 Hz), 8.29 (d, 1H, J=5.2 Hz)

(b) 4.00 ml (78.1 mmol) of bromine was dropwise added to a solution having 8.21 g (46.4 mmol) of 4-trifluoromethyl-2-methoxypyridine obtained in Step (a) and 7.98 g (97.3 mmol) of sodium acetate dissolved in 15 ml of acetic acid, followed by stirring for 4 days. A potassium hydroxide aqueous solution was added to terminate the reaction, followed by extraction with diethyl ether. The organic layer was dried over anhydrous sodium sulfate and subjected to filtration on the pad of a silica gel cake. The solvent was distilled off under reduced pressure to obtain 5.81 g of a mixture of 5-bromo-4-trifluoromethyl-2-methoxypyridine and the starting material 4-trifluoromethyl-2-methoxypyridine (molar ratio 55:45).

$^1$H-NMR (CDCl$_3$, 400 MHz): δ (ppm)=3.94 (s, 3H), 7.03 (s, 1H), 8.37 (s, 1H)

c) 17.1 ml of n-butyllithium (1.57 mol/l hexane solution) was dropwise added at 0° C. to a solution having 3.80 ml (27.1 mmol) of diisopropylamine dissolved in 50 ml of tetrahydrofuran, followed by stirring for 30 minutes. The solution was cooled to −78° C., and a solution having 5.81 g of the mixture of 5-bromo-4-trifluoromethyl-2-methoxypyridine and 4-trifluoromethyl-2-methoxypyridine (molar ratio 55:45) obtained in Step (c) dissolved in 10 ml of tetrahydrofuran was added, followed by stirring for 45 minutes to prepare a mixture of 5-bromo-4-trifluoromethyl-2-methoxy-3-pyridyllithium and 4-trifluoromethyl-2-methoxy-3-pyridyllithium. A solution having 5.51 g (26.2 mmol) of 2,3,4-trimethoxy-6-methylbenzaldehyde dissolved in 15 ml of tetrahydrofuran was added, followed by stirring for 1 hour. Water was added to the mixture to terminate the reaction, and tetrahydrofuran was distilled off under reduced pressure. After extraction with ethyl acetate, the organic layer was dried over anhydrous sodium sulfate and subjected to filtration, and the solvent was distilled off under reduced pressure. The crude product was purified by silica gel column chromatography to obtain 5.02 g of (2,3,4-trimethoxy-6-methylphenyl)(5-bromo-4-trifluoromethyl-2-methoxy-3-pyridyl)methanol.

$^1$H-NMR (CDCl$_3$, 400 MHz): δ (ppm)=2.35 (s, 3H), 3.29 (s, 3H), 3.74 (s, 3H), 3.82 (s, 3H), 3.92 (s, 3H), 4.87 (d, 1H, J=10.8 Hz), 6.21 (d, 1H, J=10.8 Hz), 6.51 (s, 1H), 8.31 (s, 1H)

(d) 20.0 g (230 mmol) of manganese dioxide was added to a solution having 4.80 g (10.3 mmol) of (2,3,4-trimethoxy-6-methylphenyl)(5-bromo-4-trifluoromethyl-2-methoxy-3-pyridyl)methanol obtained in Step (c) dissolved in 110 ml of toluene, followed by stirring under reflux with heating for 1 hour. After cooling to room temperature, the mixture was subjected to filtration on the pad of celite and the solvent was distilled off under reduced pressure. The crude product was purified by silica gel column chromatography to obtain 3.93 g (yield: 82%) of 3-(2,3,4-trimethoxy-6-methylbenzoyl)-5-bromo-4-trifluoromethyl-2-methoxypyridine (Compound No. 31).

$^1$H-NMR (CDCl$_3$, 400 MHz): δ (ppm)=2.57 (s, 3H), 3.36 (s, 3H), 3.75 (s, 3H), 3.86 (s, 3H), 3.93 (s, 3H), 6.59 (s, 1H), 8.38 (s, 1H)

(e) 3.80 ml (3.80 mmol) of dimethylzinc (1.0 mol/l hexane solution) was dropwise added at 0° C. to a solution having 0.60 g (1.29 mmol) of 3-(2,3,4-trimethoxy-6-methylbenzoyl)-5-bromo-4-trifluoromethyl-2-methoxypyridine obtained in Step (d) and 0.10 g (0.09 mmol) of tetrakis(triphenylphosphine)palladium dissolved in 10 ml of tetrahydrofuran, and the temperature was increased naturally, followed by stirring at room temperature for 8 days. Water was added to terminate the reaction, and tetrahydrofuran was distilled off under reduced pressure. After extraction with ethyl acetate, the organic layer was dried over anhydrous sodium sulfate and subjected to filtration, and the solvent was distilled off under reduced pressure. The crude product was purified by silica gel column chromatography to obtain 0.50 g (yield: 96%) of 3-(2,3,4-trimethoxy-6-methylbenzoyl)-4-trifluoromethyl-2-methoxy-5-methylpyridine.

$^1$H-NMR (CDCl$_3$, 400 MHz): δ (ppm)=2.41 (s, 3H), 2.56 (s, 3H), 3.29 (s, 3H), 3.74 (s, 3H), 3.83 (s, 3H), 3.91 (s, 3H), 6.58 (s, 1H), 8.05 (s, 1H)

Preparation Example 6

Preparation of 4-(2,3,4-trimethoxy-6-methylbenzoyl)-2,5-dichloro-3-trifluoromethylpyridine (Compound No. 39)

(a) 17 ml (25 mmol) of n-butyllithium (1.5 mol/l hexane solution) was dropwise added at 0° C. to a solution having 3.6 ml (25 mmol) of diisopropylamine dissolved in 60 ml of diethyl ether, followed by stirring for 45 minutes. The solution was cooled to −78° C., and a solution having 6.0 g (24 mmol) of 2,3,6-trichloro-5-trifluoromethylpyridine dissolved in 8 ml of diethyl ether was added, followed by stirring for 25 minutes to prepare 2,3,6-trichloro-5-trifluoromethyl-4-pyridyllithium, and then a solution having 5.0 g (24 mmol) of 2,3,4-trimethoxy-6-methylbenzaldehyde dissolved in 12 ml of toluene was added, followed by stirring for 1 hour. 30 ml of water was added to the mixture to terminate the reaction, and the aqueous layer was extracted with ethyl acetate. Then, the organic layer was dried over anhydrous sodium sulfate and subjected to filtration, and the solvent was distilled off under reduced pressure to obtain (2,3,4-trimethoxy-6-methylphenyl)(2,3,6-trichloro-5-trifluoromethyl-4-pyridyl)methanol (melting point 131 to 135° C.).

(b) 2.7 ml (19 mmol) of triethylamine and 0.9 g of 5% palladium carbon were added to a solution having 2,3,4-trimethoxy-6-methylphenyl)(2,3,6-trichloro-5-trifluoromethyl-4-pyridyl)methanol obtained in Step (a) dissolved in 200 ml of methanol, followed by stirring under a hydrogen atmosphere for 14 hours. The mixture was subjected to filtration, 30 ml of water was added, and methanol was distilled off under reduced pressure. After extraction with ethyl acetate, the organic layer was dried over anhydrous sodium sulfate and subjected to filtration, and the solvent was distilled off under reduced pressure. The crude product was purified by silica gel column chromatography to obtain 2.38 g (yield: 24%) of (2,3,4-trimethoxy-6-methylphenyl)(2,5-dichloro-3-trifluoromethyl-4-pyridyl)methanol (melting point 162 to 165° C.).

(c) 14 g of manganese dioxide was added to a solution having 3.5 g (8.2 mmol) of (2,3,4-trimethoxy-6-methylphenyl)(2,5-dichloro-3-trifluoromethyl-4-pyridyl)methanol obtained in Step (b) dissolved in 100 ml of toluene, followed by stirring under reflux with heating for 6 hours. The mixture was cooled and then subjected to filtration, and toluene was distilled off under reduced pressure. The crude product was purified by silica gel column chromatography to obtain 3.1 g (yield: 89%) of 4-(2,3,4-trimethoxy-6-methylbenzoyl)-2,5-dichloro-3-trifluoromethylpyridine (melting point 106 to 109° C.).

Preparation Example 7

Preparation of 4-(2,3,4-trimethoxy-6-methylbenzoyl)-2-chloro-3-trifluoromethyl-5-methoxypyridine (Compound No. 40)

(a) 70.0 ml (106 mmol) of n-butyllithium (1.5 mol/l hexane solution) was dropwise added at 0° C. to a diethyl ether 120 ml solution of 15.0 ml (107 mmol) of diisopropylamine, followed by stirring for 1 hour. The solution was cooled to −78° C., and a diethyl ether 10 ml solution of 22.1 g (102 mmol) of 2,3-dichloro-5-trifluoromethylpyridine was added, followed by stirring for 30 minutes to prepare 2,3-dichloro-5-trifluoromethyl-4-pyridyllithium, and then a toluene 40 ml solution of 21.0 g (100 mmol) of 2,3,4-trimethoxy-6-methylbenzaldehyde was added, followed by stirring for 2 hours. 30 ml of water was added to the mixture to terminate the reaction, and the aqueous layer was extracted with ethyl acetate. Then, the organic layer was dried over anhydrous sodium sulfate and subjected to filtration, and the solvent was distilled off under reduced pressure. The crude product was purified by silica gel column chromatography to obtain 24.8 g (yield: 58%) of (2,3,4-trimethoxy-6-methylphenyl)(2,3-dichloro-5-trifluoromethyl-4-pyridyl)methanol (melting point 95 to 98° C.).

(b) 2.1 g of 5% palladium carbon was added to a methanol 200 ml solution of 24.8 g (58.1 mmol) of (2,3,4-trimethoxy-6-methylphenyl)(2,3-dichloro-5-trifluoromethyl-4-pyridyl)methanol obtained in Step (a) and 9.50 ml (68.2 mmol) of triethylamine, followed by stirring under hydrogen atmosphere for 4 hours. The mixture was subjected to filtration, 50 ml of water was added, and methanol was distilled off under reduced pressure. The aqueous layer was extracted with ethyl acetate, and the organic layer was dried over anhydrous sodium sulfate and subjected to filtration, and the solvent was distilled off under reduced pressure. The crude product was purified by silica gel column chromatography to obtain 15.9 g (yield: 70%) of (2,3,4-trimethoxy-6-methylphenyl)(3-chloro-5-trifluoromethyl-4-pyridyl)methanol (melting point: 102 to 105° C.).

(c) 45 g of manganese dioxide was added to a toluene 220 ml solution of 15.9 g (40.6 mmol) of (2,3,4-trimethoxy-6-methylphenyl)(3-chloro-5-trifluoromethyl-4-pyridyl)methanol obtained in Step (b), followed by stirring under reflux with heating for 2 hours. The mixture was subjected to filtration, and the solvent was distilled off under reduced pressure to obtain 14.9 g (yield: 94%) of 4-(2,3,4-trimethoxy-6-methylbenzoyl)-3-chloro-5-trifluoromethylpyridine.

(d) 16.4 g (304 mmol) of sodium methoxide was added to a toluene 150 ml solution of 18.5 g (47.5 mmol) of 4-(2,3,4-trimethoxy-6-methylbenzoyl)-3-chloro-5-trifluoromethylpyridine obtained in Step (c) and 16.6 ml (95.4 mmol) of hexamethylphosphorous triamide, followed by stirring under reflux with heating for 30 minutes. Water was added to terminate the reaction, and the aqueous layer was extracted with ethyl acetate. Then, the organic layer was dried over anhydrous sodium sulfate and subjected to filtration, and the solvent was distilled off under reduced pressure. The crude product was purified by silica gel column chromatography to obtain 11.7 g (yield: 64%) of 4-(2,3,4-trimethoxy-6-methylbenzoyl)-3-methoxy-5-trifluoromethylpyridine (melting point: 103 to 106° C.).

(e) 6.1 g (28 mmol) of m-chloroperbenzoic acid (m-CPBA) was added at 0° C. to a chloroform 100 ml solution of 5.6 g (15 mmol) of 4-(2,3,4-trimethoxy-6-methylbenzoyl)-3-methoxy-5-trifluoromethylpyridine (Compound No. 122), followed by stirring at room temperature for 18 hours. The reaction solution was washed with a sodium hydroxide aqueous solution, and the solvent was distilled off under reduced pressure to obtain 5.8 g (yield: 99%) of 4-(2,3,4-trimethoxy-6-methylbenzoyl)-3-methoxy-5-trifluoromethylpyridine-N-oxide (melting point 128 to 134° C.).

(f) 1.8 ml (19 mmol) of phosphorus oxychloride was added at 0° C. to 4 ml of toluene and 8 ml of dimethylformamide, followed by stirring for 10 minutes, and then 4.0 g (10 mmol) of 4-(2,3,4-trimethoxy-6-methylbenzoyl)-3-methoxy-5-trifluoromethylpyridine-N-oxide was added, followed by stirring for 20 minutes. After stirring at room temperature for 2 hours, the reaction solution was charged into ice water to terminate the reaction. The aqueous layer was extracted with ethyl acetate, and then the organic layer was dried over anhydrous sodium sulfate and subjected to filtration, and the solvent was distilled off under reduced pressure. The crude product was purified by silica gel column chromatography to obtain 3.57 g (yield: 85%) of 4-(2,3,4-trimethoxy-6-methylbenzoyl)-2-chloro-3-trifluoromethyl-5-methoxypyridine (melting point 117 to 119° C.).

Preparation Example 8

Preparation of 3-(2,3,4-trimethoxy-6-methylbenzoyl)-5-chloro-2-methoxy-4-methylpyridine (Compound No. 35)

(a) 45.6 g (217 mmol) of 2,3,4-trimethoxy-6-methylbenzaldehyde was dissolved in 130 ml of dimethyl sulfoxide, and an aqueous solution (50 ml) of 5.2 g (44 mmol) of sodium dihydrogen phosphate was dropwise added over a period of 20 minutes. Then, an aqueous solution (180 ml) of 28 g (305 mmol) of sodium chlorite was dropwise added over a period of 3 hours, followed by stirring for 2 hours. A saturated sodium hydrogencarbonate aqueous solution was added until no bubbling occurred, followed by stirring for 1 hour. Then, the reaction solution was washed with 50 ml of ethyl acetate twice, and concentrated hydrochloric acid was added to make the aqueous layer acidic, followed by extraction with ethyl acetate. The organic layer was washed with a saturated sodium chloride solution, dried over anhydrous sodium sulfate and subjected to filtration, and the solvent was distilled off under reduced pressure. The obtained crystals were washed with hexane to obtain 45.6 g (yield: 93%) of 2,3,4-trimethoxy-6-methylbenzoic acid (melting point 95 to 97° C.).

$^1$HNMR: δ 2.56 (s, 3H), 3.86 (s, 3H), 3.91 (s, 3H), 4.03 (s, 3H), 6.60 (s, 1H)

(b-1) 6.8 ml (13.6 mmol) of isopropylmagnesium chloride (2M tetrahydrofuran solution) was cooled to 0° C., and a solution having 1.6 g (6.6 mmol) of 3-bromo-5-chloro-2-methoxy-4-methylpyridine dissolved in 5 ml of tetrahydrofuran was dropwise added, followed by stirring at the same temperature for 3 hours to prepare 5-chloro-2-methoxy-4-methyl-3-pyridylmagnesium chloride. The reaction solution was cooled to −78° C., and a solution having 1.2 g (13.3 mmol) of copper(I) cyanide and 1.15 g (27.1 mmol) of lithium chloride dissolved in 15 ml of tetrahydrofuran was dropwise added to prepare a 5-chloro-2-methoxy-4-methyl-3-pyridylcopper reagent. Separately, 3.2 g (14.3 mmol) of 2,3,4-trimethoxy-6-methylbenzoic acid prepared in Step (a) was subjected to reflux with heating in 7 ml of thionyl chloride for 3 hours, and the surplus thionyl chloride was distilled off under reduced pressure to prepare 2,3,4-trimethoxy-6-methylbenzoyl chloride, which was dissolved in 7 ml of tetrahydrofuran. The solution thus prepared was dropwise added at −78° C. to the above prepared pyridylcopper reagent, followed by stirring for 1 hour, and the temperature was increased to room temperature, followed by stirring further for 2 hours. Water and ammonia water were added to the reaction solution to terminate the reaction, followed by extraction with ethyl acetate. The organic layer was dried over anhydrous magnesium sulfate and subjected to filtration, and the solvent was distilled off under reduced pressure. The crude product was purified by silica gel column chromatography to obtain 2.6 g (yield: 57%) of 3-(2,3,4-trimethoxy-6-methylbenzoyl)-5-chloro-2-methoxy-4-methylpyridine (melting point 85 to 88° C.), and the compound was identified by $^1$HNMR.

(b-2) The same reaction as in Step (b-1) was carried out that 11 ml (11.0 mmol) of an isopropylmagnesium chloride 1M tetrahydrofuran solution and 2.5 g (10.6 mmol) of 3-bromo-5-chloro-2-methoxy-4-methylpyridine were used, except that 1.25 g (1.1 mmol) of tetrakistriphenylphosphine palladium was used instead of the tetrahydrofuran solution of copper(I) cyanide and lithium chloride, and that 2,3,4-trimethoxy-6-methylbenzoyl chloride prepared from 2.4 g (10.6 mmol) of 2,3,4-trimethoxy-6-methylbenzoic acid and 5 ml of thionyl chloride was dropwise added at 0° C. over a period of 2 hours, followed by stirring at the same temperature for 15 hours to obtain 1.7 g (yield: 43%) of 3-(2,3,4-trimethoxy-6-methylbenzoyl)-5-chloro-2-methoxy-4-methylpyridine, and the compound was identified by $^1$HNMR.

b-3) The same operation as in Step (b-2) was carried out except that 22 ml (22.0 mmol) of an isopropylmagnesium chloride 0.5M tetrahydrofuran solution was used instead of the isopropylmagnesium chloride 1M tetrahydrofuran solution, and 1.14 g (11.5 mmol) of copper chloride was used instead of tetrakistriphenylphosphine palladium to obtain 1.7 g (yield: 43%) of 3-(2,3,4-trimethoxy-6-methylbenzoyl)-5-chloro-2-methoxy-4-methylpyridine, and the compound was identified by $^1$HNMR.

Preparation Example 9

Preparation of 3-(2,3,4-trimethoxy-6-methylbenzoyl)-5-chloro-2-methoxy-4-methylpyridine (Compound No. 35)

(a) A solution having 5.0 g (19 mmol) of 2-bromo-3,4,5-trimethoxytoluene dissolved in 50 ml of diethyl ether was cooled to 78° C., and 15 ml (24 mmol) of n-butyllithium (1.6M hexane solution) was dropwise added, followed by stirring for 1.5 hours to form 2,3,4-trimethoxy-6-methyl-2-phenyllithium, and then 4.9 ml (43 mmol) of trimethyl borate was dropwise added, followed by stirring further for 1 hour. Diluted sulfuric acid was added to terminate the reaction, followed by stirring for 30 minutes, and water was further added. The aqueous layer was extracted with ethyl acetate, and the organic layer was washed with a saturated sodium chloride solution, dried over anhydrous magnesium sulfate and subjected to filtration, and the solvent was distilled off under reduced pressure to obtain 3.26 g (yield: 75%) of 2,3,4-trimethoxy-6-methylphenylboronic acid (melting point 99 to 102° C.).

$^1$HNMR: δ 2.52 (s, 3H), 3.83 (s, 3H), 3.88 (s, 3H), 3.94 (s, 3H), 6.56 (s, 1H)

(b) 1.0 g (4.3 mmol) of 3-bromo-5-chloro-2-methoxy-4-methylpyridine, 1.2 g (5.4 mmol) of 2,3,4-trimethoxy-6-methylphenylboronic acid, 1.8 g (13 mmol) of potassium carbonate, 46 mg (0.26 mmol) of palladium chloride, 147 mg (0.52 mmol) of tricyclohexylphosphine and 40 ml of tetrahydrofuran were put in a 200 ml autoclave, and carbon monoxide gas was injected to a pressure of 10 atm, followed by stirring at 120° C. for 20 hours. The reaction solution was subjected to filtration on the pad of celite, water was added, and tetrahydrofuran was distilled off under reduced pressure. The aqueous solution was extracted with ethyl acetate, the organic layer was dried over anhydrous magnesium sulfate and subjected to filtration, and the solvent was distilled off under reduced pressure. The crude product was purified by silica gel column chromatography to obtain 0.31 g (yield: 20%) of 3-(2,3,4-trimethoxy-6-methylbenzoyl)-5-chloro-2- methoxy-4-methylpyridine (melting point 92 to 94° C.), and the compound was identified by $^1$HNMR.

Preparation Example 10

Preparation of 3-(2,3,4-trimethoxy-6-methylbenzoyl)-5-chloro-2-methoxy-4-methylpyridine (Compound No. 35)

(a) Into a 500 ml four-necked flask equipped with a stirrer, a condenser, a thermometer and a nitrogen balloon, 5.4 g (222 mmol) of magnesium and 95 ml of tetrahydrofuran were charged, and 17.3 g (220 mmol) of isopropyl chloride was dropwise added while keeping the temperature in the system at 40° C., followed by stirring overnight. Then, while keeping the temperature in the system at 0° C. or below, a tetrahydrofuran 95 ml solution of 47.3 g (200 mmol) of 3-bromo-5-chloro-2-methoxy-4-methylpyridine was dropwise added, followed by stirring for 3 hours, and the reaction solution was dropwise added to dry ice.

The reaction solution was poured into 300 ml of water, the organic layer was separated out, and a hydrochloric acid solution was dropwise added to the aqueous layer to make it acidic, followed by extraction with diethyl ether. The solvent was distilled off under reduced pressure to obtain 26 g (yield: 65%) of 5-chloro-2-methoxy-4-methylnicotinic acid (melting point 127 to 129° C.).

(b) Into a 50 ml four-necked flask equipped with a stirred, a condenser, a thermometer and a nitrogen balloon, 1.0 g (4.96 mmol) of 5-chloro-2-methoxy-4-methylnicotinic acid, 0.9 g (4.94 mmol) of 3,4,5-trimethoxytoluene, 20 ml of 1,2-dichloroethane and 7.1 g (50.0 mmol) of phosphorus pentoxide were charged, followed by stirring under reflux for 1 hour.

The reaction solution was charged into 50 ml of water, and a sodium hydroxide aqueous solution was added to make the reaction solution alkaline, the aqueous layer was separated out, and the solvent was distilled off under reduced pressure. 5 ml of hexane was added to the obtained residue, and the precipitated crystals were subjected to filtration to obtain 0.4 g (yield: 22%) of a desired product.

Preparation Example 11

Preparation of 3-(2,3,4-trimethoxy-6-methylbenzoyl)-5-chloro-2-methoxy-4-methylpyridine (Compound No. 35)

Into a 20 ml recovery flask equipped with a reflux condenser, 1.0 g (5.0 mmol) of 5-chloro-2-methoxy-4-methylnicotinic acid, 10 g of 1,2-dichloroethane and 0.62 g (5.0 mmol) of oxalyl chloride were charged, followed by stirring at 25° C. for 20 minutes, and the mixture was heated at from 60° C. to 65° C. for 2 hours. After the reaction mixture was cooled to 25° C., 0.80 g (4.4 mmol) of 3,4,5-trimethoxytoluene and 0.70 g (5.2 mmol) of anhydrous aluminum chloride were added to the reaction mixture, followed by stirring at 25° C. for 3 hours.

Water and ethyl acetate were added to the reaction mixture, followed by extraction and liquid-liquid separation, and then the organic layer was dried over sodium sulfate and the solvent was distilled off under reduced pressure. n-Hexane was added to the precipitated solid, followed by filtration and drying to obtain 0.66 g (yield: 36.1%) of a desired product.

Preparation Example 12

Preparation of 3-(2,3,4-trimethoxy-6-methylbenzoyl)-5-chloro-2-methoxy-4-methylpyridine (Compound No. 35)

(a) 10 ml of thionyl chloride was added to 6.0 g (26.6 mmol) of 2,3,4-trimethoxy-6-methylbenzoic acid, followed by stirring under reflux with heating for 4 hours, and the surplus thionyl chloride was distilled off under reduced pressure. 20 ml of toluene, 8 ml of acetonitrile and 3.1 g (34.5 mmol) of copper(I) cyanide were added, followed by stirring under reflux with heating for 16 hours. After cooling to room temperature, the reaction solution was subjected to filtration on the pad of celite, and the solvent was distilled off under reduced pressure. The crude product was purified by silica gel column chromatography to obtain 2.8 g (yield: 45%) of 2,3,4-trimethoxy-6-methylbenzoyl cyanide.

$^1$HNMR: δ 2.44 (s, 3H), 3.85 (s, 3H), 3.95 (s, 3H), 4.14 (s, 3H), 6.53 (s, 1H)

(b) A solution having 1.9 g (8.0 mmol) of 2,3,4-trimethoxy-6-methylbenzoyl cyanide dissolved in 20 ml of tetrahydrofuran was cooled to −10° C., and 0.32 g (0.91 mmol) of iron(III) acetylacetonate were added, followed by stirring for 20 minutes. In another reactor, 4 ml of tetrahydrofuran was added to 4.1 ml (8.2 mmol) of an isopropylmagnesium chloride 2M tetrahydrofuran solution and the mixture was cooled to 0° C., and a solution having 1.0 g (4.2 mmol) of 3-bromo-5-chloro-2-methoxy-4-methylpyridine dissolved in 5 ml of tetrahydrofuran was dropwise added, followed by stirring for 3 hours to form 5-chloro-2-methoxy-4-methyl-3-pyridylmagnesium chloride. The pyridylmagnesium chloride solution thus prepared was dropwise added to the above prepared 2,3,4-trimethoxy-6-methylbenzoyl cyanide/iron mixed solution, followed by stirring for 3 hours. A 10% ammonium chloride aqueous solution was added to the reaction solution to terminate the reaction, followed by extraction with ethyl acetate. The organic layer was washed with a saturated sodium chloride solution, dried over anhydrous magnesium sulfate and subjected to filtration, and the solvent was distilled off under reduced pressure. The crude product was purified by silica gel column chromatography to obtain 1.7 g (yield: 58%) of a desired product.

Intermediate Preparation Example 1

(a) Into a 2 L four-necked flask equipped a stirrer, a thermometer and a gas introduction tube (inlet), 324 g (3.00 mol) of 2-amino-4-methylpyridine and 485 g of methanol were charged and mixed for dissolution, and while keeping the temperature in the system at from 10 to 30° C., 361.4 g (9.90 mol) of hydrogen chloride gas was introduced over a period of one and a half hours.

Then, in a 2 L four-necked flask equipped with a stirrer, a thermometer, a dropping funnel and an introduction tube (outlet) equipped with a bubble counter having a gas generation apparatus and a diazotization apparatus connected, 414 g (6.00 mol) of sodium nitrite, 211 g (6.60 mol) of methanol and 454 g of water were mixed, and 812.4 g (3.15 mol) of a 38% sulfuric acid aqueous solution was dropwise added over a period of 5 hours while keeping the temperature in the system at from 20 to 30° C.

In the methyl nitrite generation apparatus, simultaneously with dropwise addition of the 38% sulfuric acid aqueous solution, methyl nitrite gas in an equivalent amount was generated and introduced to the diazotization apparatus through the bubble counter.

Further, for diazotization, the reaction apparatus was cooled with water so that the temperature in the system would be kept at from 20 to 30° C.

After completion of the introduction of the methyl nitrite gas, stirring was carried out at the same temperature for 13 hours and the reaction was completed.

After methanol was distilled off under reduced pressure, 648 g of water was charged, and 518 g of a 40% sodium hydroxide aqueous solution was dropwise added at 30° C. or below to adjust the pH in the system to 12.

The formed oil was extracted with 910 g of diethyl ether, the aqueous layer was separated out, and the solvent was distilled off under reduced pressure to obtain 375.3 g of an oil. The oil (crude product) had a composition comprising 70.7% (yield: 69.5%) of 2-chloro-4-methylpyridine, 26.6% (yield: 27.2%) of 2-methoxy-4-methylpyridine and 2.6% of 2-amino-4-methylpyridine.

(b) Into a 2 L four-necked flask equipped with a stirrer, a thermometer, a condenser and a dropping funnel, 356 g of methanol was charged, and 237.6 g (4.4 mol) of sodium methoxide was charged with stirring while keeping the temperature at 50° C. or below. Then, while keeping the temperature in the system at from 60 to 70° C., 375.3 g of crude 2-chloro-4-methylpyridine (70.7%, 2.2 mol) obtained in the above Step was dropwise added over a period of 3 hours.

After completion of the dropwise addition, reflux with heating was carried out for 3 hours while distilling methanol off (the amount of methanol distilled off over 3 hours was 120 g).

After completion of the reaction, methanol remaining in the system was distilled off under reduced pressure, and 750 g of water was charged, so that the inorganic salt was dissolved.

The formed oil was extracted with 1,050 g of diethyl ether, the aqueous layer was separated out, and the solvent was distilled off under reduced pressure to obtain 370 g of an oil (crude product). The purity of the obtained 2-methoxy-4-methylpyridine was 95% (two step yield from 2-amino-4-methylpyridine: 95%).

Intermediate Preparation Example 2

Preparation of
5-chloro-4-methyl-2-methoxy-nicotinic acid (a) Preparation of a mixture of 4,4-dicyano-3-methyl-3-butenal-dimethylacetal and 1,1-dicyano-4-methoxy-2-methyl-1,3-butadiene 2.28 g (37 mmol) of acetic acid was added to a toluene 100 ml solution of 3.15 g (37 mmol) of piperidine, followed by stirring at room temperature for 1 hour, and a toluene 20 ml solution of 49.3 g (373 mmol) of acetylacetaldehyde dimethyl acetal was added. Further, a toluene 30 ml solution of 24.65 g (373 mmol) of malononitrile was slowly added over a period of 20 minutes, followed by stirring at room temperature for 5 days. The reaction mixture was washed with 50 ml of water and dried over magnesium sulfate, and the solvent was distilled off under reduced pressure to obtain 69.35 g of a mixture of 4,4-dicyano-3-methyl-3-butenol-dimethylacetal and 1,1-dicyano-4-methoxy-2-methyl-1,3-butadiene.

(b) Preparation of 3-cyano-4-methylpyridone (a) 69.35 g of the mixture of 4,4-dicyano-3-methyl-3-butenal-dimethylacetal and 1,1-dicyano-4-methoxy-2-methyl-1,3-butadiene obtained in Step (a) was slowly added to 113 g of concentrated sulfuric acid over a period of 3 hours so that the temperature would not exceed 30° C. After stirring at room temperature for 20 minutes, the temperature was increased to 50° C., and stirring was carried out at the same temperature for 2 hours. After the reaction mixture was left to stand to cool, it was slowly poured into water ice (500 ml), the obtained crystals were collected by filtration and the crystals were washed with 100 ml of water. The crystals were air-dried for 1 week and further dried at 70° C. under reduced pressure for 8 hours to obtain 34.2 g (two step yield: 68%) of crude crystals of 3-cyano-4-methylpyridone.

$^1$H-NMR (400 MHz, DMSO-d6): δ (ppm) 2.35 (s, 3H) 6.29 (d, J=6.4 Hz, 1H), 7.64 (d, J=6.4 Hz, 1H)

(c) Preparation of 2-chloro-3-cyano-4-methylpyridine 14 g (104 mmol) of 3-cyano-4-methylpyridone was slowly added to a mixture of 6.52 g (31.3 mmol) of phosphorus pentachloride and 30 ml (48 g, 313 mmol) of phosphorus oxychloride, followed by stirring at room temperature for 70 minutes and then under reflux with heating for 2 hours. After the reaction mixture was left to stand to cool, it was poured into ice water (400 ml) so that the surplus reagent was decomposed, followed by extraction with 100 ml of dichloromethane three times. The dichloromethane solution was washed with 100 ml of a saturated sodium chloride solution and dried over magnesium sulfate, and the solvent was distilled off under reduced pressure to obtain 15.1 g of crude crystals of 2-chloro-3-cyano-4-methylpyridine. $^1$H-NMR (400 MHz, DMSO-d6): δ (ppm) 2.86 (s, 3H), 7.89 (d, J=5.6 Hz, 1H) 8.86 (d, J=5.6 Hz, 1H)

(d) Preparation of 3-cyano-4-methyl-2-methoxypyridine 15.1 g of the crude crystals of 2-chloro-3-cyano-4-methylpyridine obtained in (c) was dissolved in 150 ml of anhydrous methanol, and 24.9 g (129 mmol) of a methanol solution of 28% sodium methoxide was added, followed by stirring at room temperature for 2 days. The reaction mixture was poured into 200 ml of a saturated sodium chloride solution, followed by extraction with 100 ml of ethyl acetate three times. The ethyl acetate solution was dried over magnesium sulfate and subjected to filtration through a celite/silica gel column, and the column was sufficiently washed with ethyl acetate. The filtrate and the washing liquid were put together, and the solvent was distilled off under reduced pressure to obtain 14.04 g of crude crystals of 3-cyano-4-methyl-2-methoxypyridine.

$^1$H-NMR (400 MHz, CDCl$_3$): δ (ppm) 2.51 (s, 3H), 4.03 (s, 3H) 6.84 (d, J=5.2 Hz, 1H), 8.18 (d, J=5.2 Hz, 1H)

(e) Preparation of 5-chloro-3-cyano-4-methyl-2-methoxypyridine 14.04 g (95 mmol) of 3-cyano-4-methyl-2-methoxypyridine obtained in (d) was dissolved in 100 ml of dimethylformamide, and 25.4 g (190 mmol) of N-chlorosuccinimide was added, followed by stirring at room temperature for 3 days. The progress of the reaction was confirmed by thin layer chromatography and as a result, the material was confirmed to remain, and thus stirring was carried out at 50° C. for 22 hours and then at 60° C. for 22 hours. After the reaction mixture was left to stand to cool, it was poured into 300 ml of water, followed by extraction with 100 ml of ethyl acetate three times. The ethyl acetate solution was washed with 150 ml of water twice and then 100 ml of a saturated sodium chloride solution in this order, and dried over magnesium sulfate, and the solvent was distilled off under reduced pressure. The obtained residue was purified by means of a silica gel column to obtain 13.68 g (three step yield: 79%) of 5-chloro-3-cyano-4-methyl-2-methoxypyridine. $^1$H-NMR (400 MHz, CDCl$_3$): δ (ppm) 2.56 (s, 3H), 4.03 (s, 3H) 8.23 (s, 1H)

(f) Preparation of 5-chloro-3-formyl-4-methyl-2-methoxypyridine 2.47 g (13.5 mmol) of 5-chloro-3-cyano-4-methyl-2-methoxypyridine was dissolved in 50 ml of anhydrous dichloromethane, the solution was cooled to −78° C., and 20.3 ml (20.3 mmol) of a toluene solution of 1M diisobutylammonium hydride was dropwise added slowly. After stirring at −78° C. for two and a half hours, the temperature was gradually increased to room temperature, and stirring was carried out at the same temperature for three days. The obtained solution was cooled in an ice bath, and 30 ml of water was slowly added to terminate the reaction. The reaction mixture was poured into 150 ml of 1N hydrochloric acid, followed by extraction with 100 ml of dichloromethane twice. The dichloromethane solution was washed with 100 ml of a saturated sodium chloride solution and dried over magnesium sulfate, and the solvent was distilled off under reduced pressure to obtain crude 5-chloro-3-formyl-4-methyl-2-methoxypyridine.

$^1$H-NMR (400 MHz, CDCl$_3$): δ (ppm) 2.65 (s, 3H), 4.03 (s, 3H) 8.25 (s, 1H), 10.48 (s, 1H)

(g) Preparation of 5-chloro-4-methyl-2-methoxy-nicotinic acid

Crude 5-chloro-3-formyl-4-methyl-2-methoxypyridine obtained in (f) was dissolved in 14 ml of dimethyl sulfoxide, 5.7 ml of an aqueous solution of 0.33 g (2.7 mmol) of sodium dihydrogenphosphate, and 20 ml of an aqueous solution of 2.16 g of sodium chlorite (79%, 18.9 mmol) was further dropwise added slowly over a period of 3 hours. The obtained mixture was stirred at room temperature for 5 days, and 50 ml of a sodium bicarbonate aqueous solution was added, followed by stirring overnight. The obtained solution was washed with 50 ml of ethyl acetate twice, and concentrated hydrochloric acid was added to make the aqueous layer acidic, followed by extraction with 70 ml of ethyl acetate three times. The ethyl acetate solution was washed with 50 ml of a saturated sodium chloride solution and dried over magnesium sulfate, and the solvent was distilled off under reduced pressure to obtain crude crystals. The crude crystals were dissolved in 50 ml of ethyl acetate again, followed by back extraction with 50 ml of a saturated sodium bicarbonate aqueous solution twice, and concentrated hydrochloric acid was added to make the aqueous layer acidic, followed by extraction with 70 ml of ethyl acetate three times. The ethyl acetate solution was washed with 50 ml of a saturated sodium chloride solution and dried over magnesium sulfate, and the solvent was distilled off under reduced pressure to obtain white crystals. The crystals were washed with 50 ml of hexane and air-dried to obtain 0.55 g (two step yield: 20%) of 5-chloro-4-methyl-2-methoxy-nicotinic acid.

$^1$H-NMR (400 MHz, CDCl$_3$): δ (ppm) 2.46 (s, 3H), 3.99 (s, 3H) 8.16 (s, 1H)

Now, Test Examples for the present invention will be described. However, it should be understood that the present invention is by no means restricted to such specific Examples.

Test Example 1

Test on Preventive Effect Against Wheat Powdery Mildew

Wheat (cultivar: Norin-61-go) was cultivated in a plastic pot having a diameter of 7.5 cm, and when it reached 1.5-leaf stage, 10 ml of a chemical solution having each test compound adjusted to a prescribed concentration, was applied by a spray gun in an amount of 200 L/ha. After the chemical solution dried, conidia of *Erysiphe graminis* were dusted and inoculated and maintained in a constant temperature chamber at 20° C. From 6 to 8 days after the inoculation, the area of sporulation was investigated, and the disease rate was determined in accordance with the following formula, and the results are shown in Tables 1 to 53. The average lesion area in the non-treated plot was determined in the same manner as for the treated plot except that water was applied by a spray gun instead of the chemical solution.

Disease rate=(a/b)×100 a: average lesion area in the treated plot b: average lesion area in the non-treated plot Theoretical values were calculated in accordance with the Colby's formula. The fungicidal composition of the present invention has a synergistic effect regarding the test on preventive effect against wheat powdery mildew, when the experimental value is lower than the theoretical value. Theoretical values by the Colby's formula in such cases are shown in brackets in Tables 1 to 53.

TABLE 1

| Dose of | Dose of Compound No. 23 | | | |
|---|---|---|---|---|
| Fenpropimorph | 12.5 g/ha | 6.3 g/ha | 3.1 g/ha | 0 g/ha |
| 100 g/ha | 5(64) | 10(80) | 80 | 80 |
| 50 g/ha | 20(80) | 60(100) | 65(100) | 100 |
| 25 g/ha | 60(80) | 80(100) | 100 | 100 |
| 0 g/ha | 80 | 100 | 100 | |

TABLE 2

| Dose of | Dose of Compound No. 35 | | | |
|---|---|---|---|---|
| Fenpropimorph | 6.3 g/ha | 3.1 g/ha | 1.6 g/ha | 0 g/ha |
| 100 g/ha | 0(1.5) | 0(2.3) | 2(6.8) | 15 |
| 0 g/ha | 10 | 15 | 45 | |

TABLE 3

| Dose of | Dose of Compound No. 39 | | | |
|---|---|---|---|---|
| Fenpropimorph | 12.5 g/ha | 6.3 g/ha | 3.1 g/ha | 0 g/ha |
| 100 g/ha | 10(28) | 7.5(48) | 30(48) | 80 |
| 0 g/ha | 35 | 60 | 60 | |

TABLE 4

| Dose of | Dose of Compound No. 40 | | | |
|---|---|---|---|---|
| Fenpropimorph | 6.3 g/ha | 3.1 g/ha | 1.6 g/ha | 0 g/ha |
| 100 g/ha | 2.5(4.5) | 2.5(6.7) | 5.0(6.7) | 15.0 |
| 50 g/ha | 0(13.5) | 2.5(20.2) | 17.5(20.2) | 45.0 |
| 25 g/ha | 2.5(30) | 5.0(45) | 45.0 | 100 |
| 0 g/ha | 30.0 | 45.0 | 45.0 | |

TABLE 5

| Dose of | Dose of Compound No. 23 | | | |
|---|---|---|---|---|
| Kresoxim-Methyl | 12.5 g/ha | 6.3 g/ha | 3.1 g/ha | 0 g/ha |
| 100 g/ha | 0(4) | 5.0 | 15.0(5) | 5.0 |
| 50 g/ha | 2.5(12) | 7.5(15) | 7.5(15) | 15.0 |
| 25 g/ha | 0(24) | 10.0(30) | 20.0(30) | 30.0 |
| 0 g/ha | 80.0 | 100 | 100 | |

TABLE 6

| Dose of Kresoxim-Methyl | Dose of Compound No. 35 | | | |
|---|---|---|---|---|
| | 6.3 g/ha | 3.1 g/ha | 1.6 g/ha | 0 g/ha |
| 100 g/ha | 0(1) | 0(1.5) | 0(4.5) | 10 |
| 50 g/ha | 5 | 5 | 2(6.8) | 15 |
| 0 g/ha | 10 | 15 | 45 | |

TABLE 7

| Dose of Kresoxim-Methyl | Dose of Compound No. 39 | | | |
|---|---|---|---|---|
| | 12.5 g/ha | 6.3 g/ha | 3.1 g/ha | 0 g/ha |
| 100 g/ha | 0(1.7) | 0(3.0) | 2.5(3.0) | 5.0 |
| 50 g/ha | 0(5.2) | 2.5(9.0) | 2.5(9.0) | 15.0 |
| 25 g/ha | 0(10.5) | 5.0(18.0) | 30.0 | 30.0 |
| 0 g/ha | 35.0 | 60.0 | 60.0 | |

TABLE 8

| Dose of Kresoxim-Methyl | Dose of Compound No. 40 | | | |
|---|---|---|---|---|
| | 6.3 g/ha | 3.1 g/ha | 1.6 g/ha | 0 g/ha |
| 100 g/ha | 0(4.5) | 0(6.7) | 0(6.7) | 15.0 |
| 50 g/ha | 0(9.7) | 5.0(14.6) | 5.0(14.6) | 32.5 |
| 25 g/ha | 0(9.7) | 7.5(14.6) | 15.0 | 32.5 |
| 0 g/ha | 30.0 | 45.0 | 45.0 | |

TABLE 9

| Dose of Spiroxamine | Dose of Compound No. 23 | | | |
|---|---|---|---|---|
| | 12.5 g/ha | 6.3 g/ha | 3.1 g/ha | 0 g/ha |
| 100 g/ha | 0(26.0) | 7.5(32.5) | 35.0 | 32.5 |
| 50 g/ha | 15.0(36.0) | 52.5 | 80.0(45.0) | 45.0 |
| 25 g/ha | 52.5(80.0) | 80.0(100) | 80.0(100) | 100 |
| 0 g/ha | 80.0 | 100 | 100 | |

TABLE 10

| Dose of Spiroxamine | Dose of Compound No. 35 | | | |
|---|---|---|---|---|
| | 6.3 g/ha | 3.1 g/ha | 1.6 g/ha | 0 g/ha |
| 100 g/ha | 0(2) | 0(3) | 2(9) | 20 |
| 50 g/ha | 0(6) | 5(9) | 10(27) | 60 |
| 25 g/ha | 5(8) | 10(12) | 30(36) | 80 |
| 0 g/ha | 10 | 15 | 45 | |

TABLE 11

| Dose of Spiroxamine | Dose of Compound No. 39 | | | |
|---|---|---|---|---|
| | 12.5 g/ha | 6.3 g/ha | 3.1 g/ha | 0 g/ha |
| 100 g/ha | 0(11.3) | 0(19.5) | 0(19.5) | 32.5 |
| 50 g/ha | 0(15.7) | 15.0(27.0) | 15.0(27.0) | 45.0 |
| 25 g/ha | 2.5(35) | 15.0(60.0) | 20.0(60.0) | 100 |
| 0 g/ha | 35.0 | 60.0 | 60.0 | |

TABLE 12

| Dose of Spiroxamine | Dose of Compound No. 40 | | | |
|---|---|---|---|---|
| | 6.3 g/ha | 3.1 g/ha | 1.6 g/ha | 0 g/ha |
| 100 g/ha | 0(5.2) | 0(7.8) | 2.5(7.8) | 17.5 |
| 50 g/ha | 0(24.0) | 17.5(36.0) | 20.0(36.0) | 80.0 |
| 25 g/ha | 0(30.0) | 7.5(45.0) | 35.0(45.0) | 100 |
| 0 g/ha | 30.0 | 45.0 | 45.0 | |

TABLE 13

| Dose of Epoxiconazole | Dose of Compound No. 23 | | | |
|---|---|---|---|---|
| | 12.5 g/ha | 6.3 g/ha | 3.1 g/ha | 0 g/ha |
| 3.1 g/ha | 35(36) | 20(60) | 45(60) | 60 |
| 1.6 g/ha | 55(60) | 35(100) | 60(100) | 100 |
| 0 g/ha | 60 | 100 | 100 | |

TABLE 14

| Dose of Epoxiconazole | Dose of Compound No. 35 | | | |
|---|---|---|---|---|
| | 6.3 g/ha | 3.1 g/ha | 1.6 g/ha | 0 g/ha |
| 6.3 g/ha | 0(4.5) | 0(6.8) | 10(20.3) | 45 |
| 3.1 g/ha | 0(10) | 15 | 30(45) | 100 |
| 1.6 g/ha | 2(10) | 10(15) | 20(45) | 100 |
| 0 g/ha | 10 | 15 | 45 | |

TABLE 15

| Dose of Epoxiconazole | Dose of Compound No. 39 | | | |
|---|---|---|---|---|
| | 12.5 g/ha | 6.3 g/ha | 3.1 g/ha | 0 g/ha |
| 6.3 g/ha | 0(1.5) | 0(3.2) | 15.0 | 5.0 |
| 3.1 g/ha | 2.5(18.0) | 15.0(39.0) | 20.0(48.0) | 60.0 |
| 1.6 g/ha | 7.5(30.0) | 20.0(65.0) | 65.0(80.0) | 100 |
| 0 g/ha | 30.0 | 65.0 | 80.0 | |

TABLE 16

| Dose of Epoxiconazole | Dose of Compound No. 40 | | | |
|---|---|---|---|---|
| | 6.3 g/ha | 3.1 g/ha | 1.6 g/ha | 0 g/ha |
| 6.3 g/ha | 2.5(30.0) | 2.5(45.0) | 30.0(45.0) | 100 |
| 3.1 g/ha | 7.5(30.0) | 60.0 | 45.0 | 100 |
| 0 g/ha | 30.0 | 45.0 | 45.0 | |

TABLE 17

| Dose of Tebuconazole | Dose of Compound No. 23 | | | |
|---|---|---|---|---|
| | 12.5 g/ha | 6.3 g/ha | 3.1 g/ha | 0 g/ha |
| 12.5 g/ha | 15.0(48.0) | 30.0(80.0) | 55.0(80.0) | 80.0 |
| 6.3 g/ha | 55.0(60.0) | 35.0(100) | 52.5(100) | 100 |
| 3.1 g/ha | 45.0(60.0) | 65.0(100) | 80.0(100) | 100 |
| 0 g/ha | 60.0 | 100 | 100 | |

TABLE 18

| Dose of Tebuconazole | Dose of Compound No. 35 | | |
|---|---|---|---|
| | 6.3 g/ha | 1.6 g/ha | 0 g/ha |
| 12.5 g/ha | 0(4.5) | 20(20.3) | 45 |
| 6.3 g/ha | 0(6) | 30 | 60 |
| 3.1 g/ha | 5(8) | 30(36) | 80 |
| 0 g/ha | 10 | 45 | |

TABLE 19

| Dose of Tebuconazole | Dose of Compound No. 39 | | | |
|---|---|---|---|---|
| | 12.5 g/ha | 6.3 g/ha | 3.1 g/ha | 0 g/ha |
| 12.5 g/ha | 5.0(24.0) | 5.0(52.0) | 45.0(64.0) | 80.0 |
| 6.3 g/ha | 5.0(30.0) | 7.5(65.0) | 7.5(80.0) | 100 |
| 3.1 g/ha | 5.0(30.0) | 10.0(65.0) | 20.0(80.0) | 100 |
| 0 g/ha | 30.0 | 65.0 | 80.0 | |

TABLE 20

| Dose of Tebuconazole | Dose of Compound No. 40 | | |
|---|---|---|---|
| | 6.3 g/ha | 3.1 g/ha | 0 g/ha |
| 12.5 g/ha | 15(24) | 30(36) | 80 |
| 6.3 g/ha | 20(24) | 30(36) | 80 |
| 0 g/ha | 30 | 45 | |

TABLE 21

| Dose of Quinoxyfen | Dose of Compound No. 23 | | | |
|---|---|---|---|---|
| | 12.5 g/ha | 6.3 g/ha | 3.1 g/ha | 0 g/ha |
| 6.3 g/ha | 2.5(10.5) | 15.0(17.5) | 17.5 | 17.5 |
| 1.6 g/ha | 5.0(48.0) | 65.0(80.0) | 55.0(80.0) | 80.0 |
| 0 g/ha | 60.0 | 100 | 100 | |

TABLE 22

| Dose of Quinoxyfen | Dose of Compound No. 35 | | | |
|---|---|---|---|---|
| | 6.3 g/ha | 3.1 g/ha | 1.6 g/ha | 0 g/ha |
| 6.3 g/ha | 0(0.5) | 0(1.1) | 0(1.4) | 2.4 |
| 3.1 g/ha | 2.4 | 2.4(3.2) | 0(4.3) | 7.3 |
| 1.6 g/ha | 2.4(8.6) | 0(19.4) | 0(25.9) | 44.1 |
| 0 g/ha | 19.6 | 44.1 | 58.8 | |

TABLE 23

| Dose of Quinoxyfen | Dose of Compound No. 39 | | | |
|---|---|---|---|---|
| | 12.5 g/ha | 6.3 g/ha | 3.1 g/ha | 0 g/ha |
| 6.3 g/ha | 0(5.2) | 2.5(11.3) | 2.5(14) | 17.5 |
| 3.1 g/ha | 2.5(6) | 7.5(13.0) | 20.0 | 20.0 |
| 1.6 g/ha | 5.0(24) | 5.0(52.0) | 35.0(64.0) | 80.0 |
| 0 g/ha | 30.0 | 65.0 | 80.0 | |

TABLE 24

| Dose of Quinoxyfen | Dose of Compound No. 40 | | | |
|---|---|---|---|---|
| | 6.3 g/ha | 3.1 g/ha | 1.6 g/ha | 0 g/ha |
| 6.3 g/ha | 0(9.0) | 2.5(13.5) | 5.0(13.5) | 30.0 |
| 3.1 g/ha | 0(9.0) | 5.0(13.5) | 10.0(13.5) | 30.0 |
| 1.6 g/ha | 2.5(18.0) | 20.0(27.0) | 20.0(27.0) | 60.0 |
| 0 g/ha | 30.0 | 45.0 | 45.0 | |

TABLE 25

| Dose of Metrafenone | Dose of Compound No. 35 | | | |
|---|---|---|---|---|
| | 6.3 g/ha | 3.1 g/ha | 1.6 g/ha | 0 g/ha |
| 12.5 g/ha | 17.5(36.0) | 20.0(60.0) | 45.0(60.0) | 60.0 |
| 6.3 g/ha | 20.0(48.0) | 35.0(80.0) | 45.0(80.0) | 80.0 |
| 3.1 g/ha | 32.5(60.0) | 35.0(100) | 80.0(100) | 100 |
| 0 g/ha | 60.0 | 100 | 100 | |

TABLE 26

| Dose of Propiconazole | Dose of Compound No. 23 | | |
|---|---|---|---|
| | 6.3 g/ha | 3.1 g/ha | 0 g/ha |
| 6.3 g/ha | 0(1) | 0(6) | 20 |
| 3.1 g/ha | 0(5) | 10(30) | 100 |
| 0 g/ha | 5 | 30 | |

TABLE 27

| Dose of Propiconazole | Dose of Compound No. 35 | | | |
|---|---|---|---|---|
| | 6.3 g/ha | 3.1 g/ha | 1.6 g/ha | 0 g/ha |
| 12.5 g/ha | 0(0.8) | 0(2.2) | 0(7.0) | 11.6 |
| 6.3 g/ha | 6.7 | 4.2(11.5) | 9.1(36.8) | 60.7 |
| 3.1 g/ha | 9.0 | 11.6(19.0) | 46.0(60.7) | 100 |
| 0 g/ha | 6.7 | 19.0 | 60.7 | |

TABLE 28

| Dose of Propiconazole | Dose of Compound No. 39 | | |
|---|---|---|---|
| | 6.3 g/ha | 3.1 g/ha | 0 g/ha |
| 6.3 g/ha | 0(3.5) | 0(3.5) | 20.0 |
| 3.1 g/ha | 0(17.5) | 2.5(17.5) | 100 |
| 0 g/ha | 17.5 | 17.5 | |

TABLE 29

| Dose of Propiconazole | Dose of Compound No. 40 | | |
|---|---|---|---|
| | 3.1 g/ha | 1.6 g/ha | 0 g/ha |
| 6.3 g/ha | 0(4) | 0(1) | 20 |
| 3.1 g/ha | 0(20) | 7.5 | 100 |
| 0 g/ha | 20 | 5 | |

TABLE 30

| Dose of Triadimenol | Dose of Compound No. 23 | | |
|---|---|---|---|
| | 6.3 g/ha | 3.1 g/ha | 0 g/ha |
| 6.3 g/ha | 0(27.0) | 0(45.0) | 45.0 |
| 3.1 g/ha | 5.0(39.0) | 7.5(65.0) | 65.0 |
| 0 g/ha | 60.0 | 100 | |

TABLE 31

| Dose of Triadimenol | Dose of Compound No. 35 | | | |
|---|---|---|---|---|
| | 6.3 g/ha | 3.1 g/ha | 1.6 g/ha | 0 g/ha |
| 12.5 g/ha | 0(1.3) | 0(3.6) | 0(11.5) | 19.0 |
| 6.3 g/ha | 6.7 | 4.2(10.6) | 6.7(33.9) | 55.8 |
| 0 g/ha | 6.7 | 19 | 60.7 | |

TABLE 32

| Dose of Triadimenol | Dose of Compound No. 39 | | |
|---|---|---|---|
| | 6.3 g/ha | 3.1 g/ha | 0 g/ha |
| 6.3 g/ha | 5(13.5) | 2.5(29.3) | 45.0 |
| 3.1 g/ha | 30.0 | 17.5(42.3) | 65.0 |
| 0 g/ha | 30.0 | 65.0 | |

TABLE 33

| Dose of Triadimenol | Dose of Compound No. 40 | | |
|---|---|---|---|
| | 3.1 g/ha | 1.6 g/ha | 0 g/ha |
| 6.3 g/ha | 0(9) | 5(20.3) | 45 |
| 3.1 g/ha | 0(13) | 15(29.3) | 65 |
| 0 g/ha | 20 | 45 | |

TABLE 34

| Dose of Cyproconazole | Dose of Compound No. 23 | | |
|---|---|---|---|
| | 6.3 g/ha | 3.1 g/ha | 0 g/ha |
| 6.3 g/ha | 0(0.75) | 0(4.5) | 15 |
| 3.1 g/ha | 0(4) | 10(24) | 80 |
| 0 g/ha | 5 | 30 | |

TABLE 35

| Dose of Cyproconazole | Dose of Compound No. 35 | | | |
|---|---|---|---|---|
| | 6.3 g/ha | 3.1 g/ha | 1.6 g/ha | 0 g/ha |
| 12.5 g/ha | 0(0.38) | 0(1.5) | 0(12.0) | 15.0 |
| 6.3 g/ha | 0(1.6) | 5.0(6.5) | 7.5(5.2) | 65.0 |
| 3.1 g/ha | 2.5(2.5) | 10.0(10.0) | 20.0(80.0) | 100 |
| 0 g/ha | 2.5 | 10.0 | 80.0 | |

TABLE 36

| Dose of Cyproconazole | Dose of Compound No. 39 | | |
|---|---|---|---|
| | 6.3 g/ha | 3.1 g/ha | 0 g/ha |
| 6.3 g/ha | 0(2.6) | 0(2.6) | 15.0 |
| 3.1 g/ha | 0(14.0) | 10.0(14.0) | 80.0 |
| 0 g/ha | 17.5 | 17.5 | |

TABLE 37

| Dose of Cyproconazole | Dose of Compound No. 40 | | |
|---|---|---|---|
| | 3.1 g/ha | 1.6 g/ha | 0 g/ha |
| 6.3 g/ha | 0(3.0) | 0(0.8) | 15.0 |
| 3.1 g/ha | 0(16.0) | 2.5(4.0) | 80.0 |
| 0 g/ha | 20.0 | 5.0 | |

TABLE 38

| Dose of Fluquinconazole | Dose of Compound No. 23 | | |
|---|---|---|---|
| | 6.3 g/ha | 3.1 g/ha | 0 g/ha |
| 200 g/ha | 5.0(4.5) | 5.0(7.5) | 7.5 |
| 100 g/ha | 5.0(6.0) | 7.5(10.0) | 10.0 |
| 50 g/ha | 5.0(18.0) | 10.0(30.0) | 30.0 |
| 0 g/ha | 60.0 | 100 | |

TABLE 39

| Dose of Fluquinconazole | Dose of Compound No. 35 | | | |
|---|---|---|---|---|
| | 6.3 g/ha | 3.1 g/ha | 1.6 g/ha | 0 g/ha |
| 400 g/ha | 0(0.06) | 2.5 | 0(2.0) | 2.5 |
| 200 g/ha | 0(0.2) | 2.5 | 2.5(6.0) | 7.5 |
| 100 g/ha | 0(0.5) | 0(2.0) | 2.5(16.0) | 20.0 |
| 0 g/ha | 2.5 | 10.0 | 80.0 | |

TABLE 40

| Dose of Fluquinconazole | Dose of Compound No. 39 | | |
|---|---|---|---|
| | 6.3 g/ha | 3.1 g/ha | 0 g/ha |
| 200 g/ha | 0(2.2) | 7.5 | 7.5 |
| 100 g/ha | 2.5(3) | 5.0(6.5) | 10.0 |
| 50 g/ha | 5.0(9.0) | 2.5(19.5) | 30.0 |
| 0 g/ha | 30.0 | 65.0 | |

TABLE 41

| Dose of Fluquinconazole | Dose of Compound No. 40 | | |
|---|---|---|---|
| | 3.1 g/ha | 1.6 g/ha | 0 g/ha |
| 50 g/ha | 0(6.0) | 10.0(13.5) | 30.0 |
| 0 g/ha | 20.0 | 45.0 | |

TABLE 42

| Dose of Fenpropidin | Dose of Compound No. 23 | | |
|---|---|---|---|
| | 6.3 g/ha | 3.1 g/ha | 0 g/ha |
| 50 g/ha | 5.0(36.0) | 7.5(60.0) | 60.0 |
| 25 g/ha | 5.0(48.0) | 80.0 | 80.0 |
| 12.5 g/ha | 65.0 | 35.0(100) | 100 |
| 0 g/ha | 60.0 | 100 | |

TABLE 43

| Dose of Fenpropidin | Dose of Compound No. 35 | | |
|---|---|---|---|
| | 3.1 g/ha | 1.6 g/ha | 0 g/ha |
| 50 g/ha | 2.5(3.0) | 2.5(9.0) | 30.0 |
| 25 g/ha | 2.5(6.0) | 7.5(18.0) | 60.0 |
| 12.5 g/ha | 2.5(6.0) | 7.5(18.0) | 60.0 |
| 0 g/ha | 10.0 | 30.0 | |

TABLE 44

| Dose of Fenpropidin | Dose of Compound No. 39 | | |
|---|---|---|---|
| | 6.3 g/ha | 3.1 g/ha | 0 g/ha |
| 50 g/ha | 7.5(18.0) | 5.0(39.0) | 60.0 |
| 25 g/ha | 20.0(24.0) | 30.0(52.0) | 80.0 |
| 12.5 g/ha | 20.0(30.0) | 45.0(65.0) | 100 |
| 0 g/ha | 30.0 | 65.0 | |

TABLE 45

| Dose of Fenpropidin | Dose of Compound No. 40 | | |
|---|---|---|---|
| | 3.1 g/ha | 1.6 g/ha | 0 g/ha |
| 50 g/ha | 0(12.0) | 5.0(27.0) | 60.0 |
| 25 g/ha | 15.0(16.0) | 2.5(36.0) | 80.0 |
| 12.5 g/ha | 17.5(20.0) | 7.5(45.0) | 100 |
| 0 g/ha | 20.0 | 45.0 | |

TABLE 46

| Dose of Metconazole | Dose of Compound No. 23 | | | |
|---|---|---|---|---|
| | 12.5 g/ha | 6.3 g/ha | 3.1 g/ha | 0 g/ha |
| 6.3 g/ha | 0(0.2) | 0(1.4) | 7.3 | 4.9 |
| 3.1 g/ha | 0(0.9) | 0(5.8) | 4.9(6.2) | 19.6 |
| 0 g/ha | 4.9 | 29.4 | 31.8 | |

TABLE 47

| Dose of Metconazole | Dose of Compound No. 35 | | | |
|---|---|---|---|---|
| | 6.3 g/ha | 3.1 g/ha | 1.6 g/ha | 0 g/ha |
| 6.3 g/ha | 0(1.0) | 0(2.2) | 2.4(2.9) | 4.9 |
| 3.1 g/ha | 0(3.8) | 4.9(8.6) | 7.5(11.5) | 19.6 |
| 1.6 g/ha | 14.7(8.6) | 17.1(19.4) | 44.1 | 44.1 |
| 0 g/ha | 19.6 | 44.1 | 58.8 | |

TABLE 48

| Dose of Metconazole | Dose of Compound No. 39 | | | |
|---|---|---|---|---|
| | 6.3 g/ha | 3.1 g/ha | 1.6 g/ha | 0 g/ha |
| 3.1 g/ha | 4.9 | 4.9(8.6) | 7.3(11.5) | 19.6 |
| 1.6 g/ha | 2.4(8.6) | 4.9(19.4) | 7.3(25.9) | 44.1 |
| 0 g/ha | 19.6 | 44.1 | 58.8 | |

TABLE 49

| Dose of Metconazole | Dose of Compound No. 40 | | |
|---|---|---|---|
| | 6.3 g/ha | 3.1 g/ha | 0 g/ha |
| 6.3 g/ha | 0(0.7) | 0(0.8) | 4.9 |
| 1.6 g/ha | 0(6.4) | 4.9(7.5) | 44.1 |
| 0 g/ha | 14.7 | 17.1 | |

TABLE 50

| Dose of Tetraconazole | Dose of Compound No. 23 | | |
|---|---|---|---|
| | 6.3 g/ha | 3.1 g/ha | 0 g/ha |
| 6.3 g/ha | 0(1.75) | 5.0(10.5) | 35.0 |
| 3.1 g/ha | 2.5(4.0) | 7.5(24.0) | 80.0 |
| 0 g/ha | 5.0 | 30.0 | |

TABLE 51

| Dose of Tetraconazole | Dose of Compound No. 35 | | |
|---|---|---|---|
| | 3.1 g/ha | 1.6 g/ha | 0 g/ha |
| 6.3 g/ha | 0(10.5) | 0(21.0) | 35.0 |
| 3.1 g/ha | 0(24.0) | 5.0(48.0) | 80.0 |
| 0 g/ha | 30.0 | 60.0 | |

TABLE 52

| Dose of Tetraconazole | Dose of Compound No. 39 | | |
|---|---|---|---|
| | 6.3 g/ha | 3.1 g/ha | 0 g/ha |
| 6.3 g/ha | 0(6.1) | 2.5(6.1) | 35.0 |
| 3.1 g/ha | 2.5(14.0) | 7.5(14.0) | 80.0 |
| 0 g/ha | 17.5 | 17.5 | |

TABLE 53

| Dose of Tetraconazole | Dose of Compound No. 40 | | |
|---|---|---|---|
| | 3.1 g/ha | 1.6 g/ha | 0 g/ha |
| 6.3 g/ha | 0(3.5) | 0(1.8) | 35.0 |
| 3.1 g/ha | 0(16.0) | 15.0(4.0) | 80.0 |
| 0 g/ha | 20.0 | 5.0 | |

Test Example 2

Test on Preventive Effect Against Cucumber Powdery Mildew

Cucumber (cultivar: Suyo) was cultivated in a plastic pot having a diameter of 7.5 cm, and when it reached 1.5-leaf stage, 10 ml of a chemical solution having the compound of the present invention adjusted to a prescribed concentration, was applied by a spray gun. After the chemical solution dried, a suspension of conidia of *Sphaerotheca cucurbitae* was sprayed and inoculated and maintained in a constant temperature chamber at 20° C. From 6 to 11 days after the inoculation, the area of sporulation was investigated, and the disease rate was determined in the same manner as in Test Example 3, and the results are shown in Tables 54 to 96. The average lesion area in the non-treated plot was determined in the same manner as for the treated plot except that water was applied by a spray gun instead of the chemical solution.

Further, theoretical values by the Colby's formula are shown in brackets in Tables 54 to 96.

TABLE 54

| Triflumizole concentration | Compound No. 23 concentration | | | |
| --- | --- | --- | --- | --- |
| | 8 ppm | 4 ppm | 2 ppm | 0 ppm |
| 31 ppm | 0(2.0) | 0(2.1) | 0(2.4) | 2.4 |
| 16 ppm | 54.3(57.9) | 64.2 | 64.2(69.1) | 69.1 |
| 0 ppm | 83.9 | 88.9 | 100 | |

TABLE 55

| Triflumizole concentration | Compound No. 35 concentration | | | |
| --- | --- | --- | --- | --- |
| | 4 ppm | 2 ppm | 1 ppm | 0 ppm |
| 31 ppm | 0(14.3) | 0(16.1) | 0(17.7) | 17.7 |
| 16 ppm | 12.6(57.3) | 70.8 | 45.5(70.8) | 70.8 |
| 0 ppm | 80.9 | 91.0 | 100 | |

TABLE 56

| Triflumizole concentration | Compound No. 39 concentration | | | |
| --- | --- | --- | --- | --- |
| | 16 ppm | 8 ppm | 4 ppm | 0 ppm |
| 16 ppm | 0(6.0) | 7.5 | 7.5(24) | 30.0 |
| 8 ppm | 5(16.0) | 17.5(24.0) | 45.0(64.0) | 80.0 |
| 0 ppm | 20.0 | 30.0 | 80.0 | |

TABLE 57

| Triflumizole concentration | Compound No. 40 concentration | | | |
| --- | --- | --- | --- | --- |
| | 4 ppm | 2 ppm | 1 ppm | 0 ppm |
| 16 ppm | 35.4(57.9) | 49.4(64.8) | 34.5(69.1) | 69.1 |
| 8 ppm | 49.7(74.5) | 74.1(83.3) | 83.9(88.9) | 88.9 |
| 0 ppm | 83.9 | 93.8 | 100 | |

TABLE 58

| Mepanipyrim concentration | Compound No. 23 concentration | |
| --- | --- | --- |
| | 8 ppm | 0 ppm |
| 16 ppm | 39.5(41.4) | 49.4 |
| 8 ppm | 59.2(83.9) | 100 |
| 4 ppm | 74.1(83.9) | 100 |
| 0 ppm | 83.9 | |

TABLE 59

| Mepanipyrim concentration | Compound No. 35 concentration | | | |
| --- | --- | --- | --- | --- |
| | 4 ppm | 2 ppm | 1 ppm | 0 ppm |
| 16 ppm | 40.4(61.3) | 60.7(69.0) | 60.7(75.8) | 75.8 |
| 8 ppm | 25.3(80.9) | 100 | 96.1(100) | 100 |
| 4 ppm | 55.6(77.7) | 85.9(87.5) | 91.0(96.1) | 96.1 |
| 0 ppm | 80.9 | 91.0 | 100 | |

TABLE 60

| Mepanipyrim concentration | Compound No. 39 concentration | | |
| --- | --- | --- | --- |
| | 16 ppm | 4 ppm | 0 ppm |
| 16 ppm | 7.5(16.0) | 45.0(64.0) | 80.0 |
| 8 ppm | 2.5(20.0) | 60.0(80.0) | 100 |
| 4 ppm | 17.5(20.0) | 60.0(80.0) | 100 |
| 0 ppm | 20.0 | 80.0 | |

TABLE 61

| Mepanipyrim concentration | Compound No. 40 concentration | |
| --- | --- | --- |
| | 4 ppm | 0 ppm |
| 16 ppm | 14.8(41.4) | 49.4 |
| 8 ppm | 64.2(83.9) | 100 |
| 0 ppm | 83.9 | |

TABLE 62

| Iminoctadine albesilate concentration | Compound No. 23 concentration | |
| --- | --- | --- |
| | 2 ppm | 0 ppm |
| 8 ppm | 79.0(83.9) | 83.9 |
| 0 ppm | 100 | |

TABLE 63

| Iminoctadine albesilate concentration | Compound No. 35 concentration | | | |
| --- | --- | --- | --- | --- |
| | 4 ppm | 2 ppm | 1 ppm | 0 ppm |
| 16 ppm | 2.5(28.6) | 15.1(32.1) | 22.8(35.3) | 35.3 |
| 8 ppm | 7.6(49.1) | 55.6 | 25.3(60.7) | 60.7 |
| 4 ppm | 7.6(69.5) | 70.8(78.2) | 91.0(85.9) | 85.9 |
| 0 ppm | 80.9 | 91.0 | 100 | |

TABLE 64

| Iminoctadine albesilate concentration | Compound No. 39 concentration | | | |
| --- | --- | --- | --- | --- |
| | 16 ppm | 8 ppm | 4 ppm | 0 ppm |
| 16 ppm | 2.5(6.0) | 7.5(9.0) | 10.0(24.0) | 30.0 |
| 8 ppm | 2.5(9.0) | 7.5(13.5) | 30.0(36.0) | 45.0 |
| 0 ppm | 20.0 | 30.0 | 80.0 | |

TABLE 65

| Iminoctadine albesilate | Compound No. 40 concentration | | | |
|---|---|---|---|---|
| concentration | 4 ppm | 2 ppm | 1 ppm | 0 ppm |
| 16 ppm | 7.4(41.4) | 19.7(46.3) | 44.4(49.4) | 49.4 |
| 4 ppm | 74.1(78.6) | 83.9(87.9) | 88.9(93.8) | 93.8 |
| 0 ppm | 83.9 | 93.8 | 100 | |

TABLE 66

| Oxpoconazole fumarate | Compound No. 35 concentration | | | |
|---|---|---|---|---|
| concentration | 4 ppm | 2 ppm | 1 ppm | 0 ppm |
| 31 ppm | 5.1(36.8) | 20.2(41.4) | 35.4(45.5) | 45.5 |
| 16 ppm | 45.5(80.9) | 75.8(91.0) | 100 | 100 |
| 8 ppm | 60.7(80.9) | 85.9(91.0) | 80.9(100) | 100 |
| 0 ppm | 80.9 | 91.0 | 100 | |

TABLE 67

| Oxpoconazole fumarate | Compound No. 39 concentration | | | |
|---|---|---|---|---|
| concentration | 16 ppm | 8 ppm | 4 ppm | 0 ppm |
| 31 ppm | 0(6.0) | 7.5(9) | 7.5(24.0) | 30.0 |
| 16 ppm | 0(12.0) | 30.0 | 45.0(48.0) | 60.0 |
| 8 ppm | 2.5(16.0) | 17.5(24.0) | 60.0(64.0) | 80.0 |
| 0 ppm | 20.0 | 30.0 | 80.0 | |

TABLE 68

| Azoxystrobin | Compound No. 23 concentration | |
|---|---|---|
| concentration | 16 ppm | 0 ppm |
| 63 ppm | 8.4(30.7) | 100 |
| 31 ppm | 10.9(30.7) | 100 |
| 0 ppm | 30.7 | |

TABLE 69

| Azoxystrobin | Compound No. 35 concentration | | | |
|---|---|---|---|---|
| concentration | 4 ppm | 2 ppm | 1 ppm | 0 ppm |
| 63 ppm | 9.3(11.7) | 65.7 | 80.4 | 100 |
| 31 ppm | 21.6 | 31.4(52.8) | 31.4(64.6) | 80.4 |
| 0 ppm | 11.7 | 65.7 | 80.4 | |

TABLE 70

| Azoxystrobin | Compound No. 39 concentration | | | |
|---|---|---|---|---|
| concentration | 16 ppm | 8 ppm | 4 ppm | 0 ppm |
| 125 ppm | 5.0(20.0) | 45.0 | 80.0 | 100 |
| 63 ppm | 7.5(20.0) | 45.0 | 45.0(80.0) | 100 |
| 31 ppm | 5.0(20.0) | 20.0(30.0) | 60.0(80.0) | 100 |
| 0 ppm | 20.0 | 30.0 | 80.0 | |

TABLE 71

| Azoxystrobin | Compound No. 40 concentration | | |
|---|---|---|---|
| concentration | 2 ppm | 1 ppm | 0 ppm |
| 63 ppm | 60.4(80.2) | 100 | 100 |
| 0 ppm | 80.2 | 100 | |

TABLE 72

| Polyoxins | Compound No. 23 concentration | | | |
|---|---|---|---|---|
| concentration | 16 ppm | 8 ppm | 4 ppm | 0 ppm |
| 125 ppm | 3.4(18.5) | 10.9(27.4) | 30.7(36.4) | 60.4 |
| 63 ppm | 5.9(30.7) | 20.8(45.5) | 30.7(60.4) | 100 |
| 31 ppm | 5.9(30.7) | 20.8(45.5) | 60.4 | 100 |
| 0 ppm | 30.7 | 45.5 | 60.4 | |

TABLE 73

| Polyoxins | Compound No. 35 concentration | | | |
|---|---|---|---|---|
| concentration | 4 ppm | 2 ppm | 1 ppm | 0 ppm |
| 125 ppm | 0(2.5) | 4.4(14.2) | 11.7(17.3) | 21.6 |
| 63 ppm | 16.7 | 31.4 | 31.4(37.0) | 46.1 |
| 31 ppm | 16.7 | 31.4(52.8) | 60.8(64.6) | 80.4 |
| 0 ppm | 11.7 | 65.7 | 80.4 | |

TABLE 74

| Polyoxins | Compound No. 39 concentration | | | |
|---|---|---|---|---|
| concentration | 16 ppm | 8 ppm | 4 ppm | 0 ppm |
| 125 ppm | 2.5(6.0) | 10.0 | 30.0 | 30.0 |
| 63 ppm | 2.5(9.0) | 20.0 | 45.0 | 45.0 |
| 31 ppm | 7.5(16.0) | 20.0(24.0) | 45.0(64.0) | 80.0 |
| 0 ppm | 20.0 | 30.0 | 80.0 | |

TABLE 75

| Polyoxins | Compound No. 40 concentration | | | |
|---|---|---|---|---|
| concentration | 4 ppm | 2 ppm | 1 ppm | 0 ppm |
| 125 ppm | 10.8(18.5) | 45.5(48.4) | 45.5(60.4) | 60.4 |
| 63 ppm | 30.7 | 30.7(80.2) | 45.5(100) | 100 |
| 31 ppm | 35.6 | 45.5(80.2) | 80.2(100) | 100 |
| 0 ppm | 30.7 | 80.2 | 100 | |

TABLE 76

| Cyazofamid | Compound No. 23 concentration | | | |
|---|---|---|---|---|
| concentration | 16 ppm | 8 ppm | 4 ppm | 0 ppm |
| 125 ppm | 18.3(30.7) | 45.5 | 80.2 | 100 |
| 63 ppm | 8.4(30.7) | 30.7(45.5) | 45.5(60.4) | 100 |
| 31 ppm | 10.9(30.7) | 30.7(45.5) | 60.4 | 100 |
| 0 ppm | 30.7 | 45.5 | 60.4 | |

TABLE 77

| Cyazofamid concentration | Compound No. 35 concentration | | | |
|---|---|---|---|---|
| | 4 ppm | 2 ppm | 1 ppm | 0 ppm |
| 125 ppm | 9.3(9.4) | 31.4(52.8) | 46.1(64.6) | 80.4 |
| 63 ppm | 11.7 | 46.1(65.7) | 80.4 | 100 |
| 0 ppm | 11.7 | 65.7 | 80.4 | |

TABLE 78

| Cyazofamid concentration | Compound No. 39 concentration | | | |
|---|---|---|---|---|
| | 16 ppm | 8 ppm | 4 ppm | 0 ppm |
| 125 ppm | 0(20) | 20(30) | 80 | 100 |
| 63 ppm | 5(20) | 65 | 100 | 100 |
| 31 ppm | 0(20) | 45 | 60(80) | 100 |
| 0 ppm | 20 | 30 | 80 | |

TABLE 79

| Cyazofamid concentration | Compound No. 40 concentration | | |
|---|---|---|---|
| | 2 ppm | 1 ppm | 0 ppm |
| 125 ppm | 100 | 65.4(100) | 100 |
| 63 ppm | 45.5(80.2) | 80.2(100) | 100 |
| 0 ppm | 80.2 | 100 | |

TABLE 80

| Chlorothalonil concentration | Compound No. 23 concentration | | |
|---|---|---|---|
| | 16 ppm | 4 ppm | 0 ppm |
| 125 ppm | 8.4(30.7) | 65.4 | 100 |
| 63 ppm | 18.3(30.7) | 80.2 | 100 |
| 31 ppm | 20.8(30.7) | 45.5(60.4) | 100 |
| 0 ppm | 30.7 | 60.4 | |

TABLE 81

| Chlorothalonil concentration | Compound No. 35 concentration | | |
|---|---|---|---|
| | 2 ppm | 1 ppm | 0 ppm |
| 125 ppm | 65.7 | 46.1(80.4) | 100 |
| 63 ppm | 55.9 | 55.9(64.6) | 80.4 |
| 31 ppm | 36.3(52.8) | 31.4(64.6) | 80.4 |
| 0 ppm | 65.7 | 80.4 | |

TABLE 82

| Chlorothalonil concentration | Compound No. 39 concentration | | | |
|---|---|---|---|---|
| | 16 ppm | 8 ppm | 4 ppm | 0 ppm |
| 125 ppm | 2.5(12.0) | 30.0 | 30.0(48.0) | 60.0 |
| 63 ppm | 2.5(16.0) | 20.0(24.0) | 30.0(64.0) | 80.0 |
| 31 ppm | 5.0(16.0) | 20.0(24.0) | 45.0(64.0) | 80.0 |
| 0 ppm | 20.0 | 30.0 | 80.0 | |

TABLE 83

| Chlorothalonil concentration | Compound No. 40 concentration | | | |
|---|---|---|---|---|
| | 4 ppm | 2 ppm | 1 ppm | 0 ppm |
| 125 ppm | 8.4(30.7) | 20.8(80.2) | 65.4(100) | 100 |
| 63 ppm | 45.5 | 45.5(80.2) | 100 | 100 |
| 31 ppm | 30.7 | 60.4(80.2) | 60.4 | 100 |
| 0 ppm | 30.7 | 80.2 | 100 | |

TABLE 84

| Imibenconazole concentration | Compound No. 23 concentration | |
|---|---|---|
| | 16 ppm | 0 ppm |
| 8 ppm | 20.8(30.7) | 100 |
| 4 ppm | 20.8(30.7) | 100 |
| 0 ppm | 30.7 | |

TABLE 85

| Imibenconazole concentration | Compound No. 35 concentration | |
|---|---|---|
| | 16 ppm | 0 ppm |
| 16 ppm | 31.4(52.8) | 65.7 |
| 4 ppm | 31.4(64.6) | 80.4 |
| 0 ppm | 80.4 | |

TABLE 86

| Imibenconazole concentration | Compound No. 39 concentration | | |
|---|---|---|---|
| | 16 ppm | 4 ppm | 0 ppm |
| 16 ppm | 5.0(12.0) | 30.0 | 60.0 |
| 8 ppm | 2.5(20.0) | 45.0(80.0) | 100 |
| 4 ppm | 2.5(20.0) | 65.0(80.0) | 100 |
| 0 ppm | 20.0 | 80.0 | |

TABLE 87

| Imibenconazole concentration | Compound No. 40 concentration | | |
|---|---|---|---|
| | 2 ppm | 1 ppm | 0 ppm |
| 16 ppm | 35.6(64.3) | 60.4(80.2) | 80.2 |
| 8 ppm | 60.4(80.2) | 80.2(100) | 100 |
| 0 ppm | 80.2 | 100 | |

TABLE 88

| Tebuconazole concentration | Compound No. 23 concentration | | |
|---|---|---|---|
| | 8 ppm | 4 ppm | 0 ppm |
| 4 ppm | 1.8(5.0) | 12.4(40.3) | 71.0 |
| 2 ppm | 3.6(4.0) | 1.8(32.3) | 56.8 |
| 0 ppm | 7.1 | 56.8 | |

TABLE 89

| Tebuconazole concentration | Compound No. 35 concentration | | |
|---|---|---|---|
| | 2 ppm | 1 ppm | 0 ppm |
| 4 ppm | 24.6 | 39.1(40.3) | 71.0 |
| 2 ppm | 7.1(8.1) | 32.0(32.3) | 56.8 |
| 0 ppm | 14.2 | 56.8 | |

TABLE 90

| Tebuconazole concentration | Compound No. 39 concentration | | |
|---|---|---|---|
| | 8 ppm | 4 ppm | 0 ppm |
| 4 ppm | 1.8(10.1) | 3.6(22.7) | 71.0 |
| 2 ppm | 3.6(8.1) | 24.9(18.2) | 56.8 |
| 0 ppm | 14.2 | 32.0 | |

TABLE 91

| Tebuconazole concentration | Compound No. 40 concentration | | |
|---|---|---|---|
| | 2 ppm | 1 ppm | 0 ppm |
| 4 ppm | 7.1(30.2) | 37.3(50.4) | 71.0 |
| 0 ppm | 42.6 | 71.0 | |

TABLE 92

| Tetraconazole concentration | Compound No. 23 concentration | |
|---|---|---|
| | 4 ppm | 0 ppm |
| 4 ppm | 21.3(32.3) | 56.8 |
| 2 ppm | 14.2(32.3) | 56.8 |
| 0 ppm | 56.8 | |

TABLE 93

| Tetraconazole concentration | Compound No. 35 concentration | | |
|---|---|---|---|
| | 2 ppm | 1 ppm | 0 ppm |
| 4 ppm | 14.2 | 14.2(32.3) | 56.8 |
| 2 ppm | 7.1(8.1) | 32.0(32.3) | 56.8 |
| 0 ppm | 14.2 | 56.8 | |

TABLE 94

| Tetraconazole concentration | Compound No. 39 concentration | | |
|---|---|---|---|
| | 8 ppm | 4 ppm | 0 ppm |
| 4 ppm | 1.8(8.1) | 39.1 | 56.8 |
| 2 ppm | 1.8(8.1) | 5.3(18.2) | 56.8 |
| 0 ppm | 14.2 | 32.0 | |

TABLE 95

| Tetraconazole concentration | Compound No. 40 concentration | | |
|---|---|---|---|
| | 2 ppm | 1 ppm | 0 ppm |
| 4 ppm | 14.2(24.2) | 5.3(40.3) | 56.8 |
| 2 ppm | 21.3(24.2) | 12.4(40.3) | 56.8 |
| 0 ppm | 42.6 | 71.0 | |

TABLE 96

| Oxpoconazole concentration | Compound No. 23 concentration | | | |
|---|---|---|---|---|
| | 16 ppm | 8 ppm | 4 ppm | 0 ppm |
| 8 ppm | 0(1.1) | 4.9(8.8) | 19.8(35.2) | 44.5 |
| 0 ppm | 2.4 | 19.8 | 79.2 | |

Now, Formulation Examples of the present invention will be described below. However, the blend ratio, type of formulation or the like of the present invention is by no means restricted to the following Examples.

Formulation Example 1

| | |
|---|---|
| (a) Kaolin | 78 parts by weight |
| (b) Condensate of β-naphthalenesulfonic acid sodium salt with formalin | 2 parts by weight |
| (c) Polyoxyethylene alkylaryl sulfate | 5 parts by weight |
| (d) Hydrated amorphous silicon dioxide | 15 parts by weight |

A mixture of the above components, the compound of the formula (I) and Epoxiconazole are mixed in a weight ratio of 8:1:1 to obtain a wettable powder.

Formulation Example 2

| | |
|---|---|
| (a) Compound of the formula (I) | 0.5 part by weight |
| (b) Epoxiconazole | 0.5 part by weight |
| (c) Bentonite | 20 parts by weight |
| (d) Kaolin | 74 parts by weight |
| (e) Sodium lignin sulfonate | 5 parts by weight |

An appropriate amount of water for granulation is added to the above components and mixed, and the mixture is granulated to obtain granules.

Formulation Example 3

| | |
|---|---|
| (a) Compound of the present invention | 2 parts by weight |
| (b) Epoxiconazole | 3 parts by weight |
| (c) Talc | 95 parts by weight |

The above components are uniformly mixed to obtain a dust.

The entire disclosures of Japanese Patent Application No. 2003-371863 filed on Oct. 31, 2003, Japanese Patent Application No. 2004-006355 filed on Jan. 14, 2004 and Japanese Patent Application No. 2004-210174 filed on Jul. 16, 2004 including specifications, claims and summaries are incorporated herein by reference in their entireties.

What is claimed is:

1. A process for producing 3-(2,3,4-trimethoxy-6-methylbenzoyl)-5-chloro-2-methoxy-4-methylpyridine or a salt thereof, comprising:
   (a) reacting 5-chloro-2-methoxy-4-methylnicotinic acid with a halogenating agent to obtain a 5-chloro-2-methoxy-4-methylnicotinic acid halide, and
   (b) subjecting the 5-chloro-2-methoxy-4-methylnicotinic acid halide obtained in (a), without isolating the acid halide, and 3,4,5-trimethoxytoluene to a Friedel-Crafts reaction in a solvent selected from the group consisting of 1,2-dichloroethane, methylene chloride, chlorobenzene, dichlorobenzene, and mixtures thereof to obtain the 3-(2,3,4-trimethoxy-6-methylbenzoyl)-5-chloro-2-methoxy-4-methylpyridine.

2. The method of claim 1, wherein the solvent is 1,2-dichloroethane.

3. The method of claim 1, wherein the solvent is methylene chloride.

4. The method of claim 1, wherein the solvent is chlorobenzene.

5. The method of claim 1, wherein the solvent is dichlorobenzene.

6. The method of claim 1, wherein (a) is conducted in an inert solvent.

7. The method of claim 6, wherein the inert solvent is selected from the group consisting of 1,2-dichloroethane, methylene chloride, chlorobenzene, dichlorobenzene and mixtures thereof.

8. The method of claim 6, wherein the inert solvent in (a) is the same as the solvent in (b).

\* \* \* \* \*